United States Patent [19]

Singh et al.

[11] Patent Number: 5,532,138

[45] Date of Patent: Jul. 2, 1996

[54] METHOD AND KITS FOR DETERMINING PEROXIDATIVELY ACTIVE CATALYSTS

[75] Inventors: Sharat Singh, San Jose; Arthur C. Switchenko, Palo Alto; Cheng-I Lin, Cupertino; Nurith Kurn, Palo Alto; Edwin F. Ullman, Atherton, all of Calif.

[73] Assignee: Behringwerke AG, Marburg, Germany

[21] Appl. No.: 263,164

[22] Filed: Jun. 21, 1994

Related U.S. Application Data

[63] Continuation of Ser. No. 951,922, Aug. 6, 1992, abandoned, which is a continuation of Ser. No. 516,022, Apr. 26, 1990, abandoned.

[51] Int. Cl.$^6$ .......................... G01N 33/546; C12Q 1/28
[52] U.S. Cl. .......................... 435/7.93; 435/7.94; 435/28; 435/9.75
[58] Field of Search .................................. 435/7.9–7.95, 435/28, 810, 975; 436/135

[56] References Cited

U.S. PATENT DOCUMENTS

| | | | |
|---|---|---|---|
| 3,527,331 | 9/1970 | Deutsch | 195/103.5 |
| 3,817,837 | 6/1974 | Rubenstein et al. | 195/103.5 R |
| 3,996,345 | 12/1976 | Ullman et al. | 424/12 |
| 4,089,747 | 5/1978 | Bruschi | 436/135 X |
| 4,233,402 | 11/1980 | Maggio et al. | 435/7 |
| 4,275,149 | 6/1981 | Litman et al. | 435/7 |
| 4,279,992 | 7/1981 | Boguslaski et al. | 435/7 |
| 4,279,993 | 7/1981 | Magers et al. | 435/14 |
| 4,299,916 | 11/1981 | Litman et al. | 435/6 |
| 4,310,626 | 1/1982 | Burkhardt et al. | 435/28 |
| 4,318,980 | 3/1982 | Boguslaski et al. | 435/7 |
| 4,391,905 | 7/1983 | Bauer | 435/14 |
| 4,391,906 | 7/1983 | Bauer | 435/14 |
| 4,427,783 | 1/1984 | Newman et al. | 435/7.93 X |
| 4,486,530 | 12/1984 | David et al. | 435/7 |
| 4,492,754 | 1/1985 | Trager et al. | 435/28 |
| 4,503,143 | 3/1985 | Gerber et al. | 435/7 |
| 4,556,640 | 12/1985 | Gantzer | 436/66 |
| 4,587,220 | 5/1986 | Mayambala-Mwanika et al. | 436/66 |
| 4,596,770 | 6/1986 | Parham et al. | 435/7 |
| 4,615,972 | 10/1986 | Gallacher | 435/28 |
| 4,672,029 | 6/1987 | Washburn et al. | 435/28 X |
| 4,680,259 | 7/1987 | Cumbo et al. | 435/25 X |
| 4,789,630 | 12/1988 | Bloch et al. | 435/7 |
| 4,845,030 | 7/1989 | Batz et al. | 435/28 |
| 4,853,328 | 8/1989 | Okazaki et al. | 435/28 |
| 4,879,214 | 11/1989 | Kornher et al. | 435/91 |
| 4,891,314 | 1/1990 | Pauly et al. | 435/28 |
| 4,895,798 | 1/1990 | Charlton et al. | 436/904 X |
| 4,978,612 | 12/1990 | Kobayashi et al. | 435/28 X |

FOREIGN PATENT DOCUMENTS

| | | |
|---|---|---|
| 0060518A1 | 9/1982 | European Pat. Off. |
| 0123902A2 | 11/1984 | European Pat. Off. |
| 0130520A1 | 1/1985 | European Pat. Off. |
| 0164008A2 | 12/1985 | European Pat. Off. |
| 0224210A1 | 6/1987 | European Pat. Off. |
| 0252747A2 | 1/1988 | European Pat. Off. |
| 1560077 | 1/1980 | United Kingdom |
| PCT/WO86/04610 | 8/1986 | WIPO |
| PCTWO86/05207 | 9/1986 | WIPO |

OTHER PUBLICATIONS

Danner, et al. *Archives of Biochemistry & Biophysics* 1973, 156, 756–763.
Weller, et al., *Archives of Biochemistry & Biophysics* 1985, 243 (2), 633–643.
Dunford, et al., *Archives of Biochemistry & Biophysics* 1986, 251 (2), 536–542.
Liem, et al., *Analytical Biochemistry* 1979, 98, 388–393.
Josephy, et al., *Carcinogenesis* 1982, 3 (10), 1227–1230.
Josephy, et al., *Biochemical Pharmacology* 1984, 33 (7), 1155–1156.
Rosalyn, et al., *Radioisotope Service, VA Hospital, New York, NY* Mar. 1960, 1157–1175.
Clark, *Oxidation Reduction Potentials of Organic Systems* 1960, 359–395 (book).
Maggio, *Enzyme–Immunoassay* 1980, 167–179 (book).

*Primary Examiner*—Mary E. Ceperley
*Attorney, Agent, or Firm*—Theodore J. Leitereg; Mark L. Bosse; Janet Kaku

[57] ABSTRACT

Methods and compositions are disclosed for determining a peroxidatively active catalyst. The methods comprise the step of detecting a substance formed by the coupling reaction of (a) the product of the peroxidatively active catalyst-catalyzed oxidation of a benzidine with (b) a coupler other than benzidine. The methods have application in a wide variety of systems including assays for analytes. Also disclosed are kits for conducting methods and assays in accordance with the present invention.

13 Claims, No Drawings

METHOD AND KITS FOR DETERMINING PEROXIDATIVELY ACTIVE CATALYSTS

This application is a continuation of patent application, U.S. Ser. No. 07/951,922, filed Aug. 6, 1992, abandoned, which is a continuation of patent application U.S. Ser. No. 07/516,022, filed Apr. 26, 1990, abandoned.

BACKGROUND OF THE INVENTION

1. Field of the Invention

The invention concerns methods and compositions for the determination of peroxidatively active catalysts, assays involving the method of the present invention, and kits for conducting such methods and assays.

The peroxidases are a group of enzymes which catalyze the oxidation of specific substrates by hydroperoxides usually hydrogen peroxide. Certain substrates, when oxidized in this way, become strong chromophors, generating intense color. The peroxidases have been widely used as labels in assay application, usually as conjugates with specific binding pair members as assay components. The presence of such a labelled component can be readily detected by adding a substrate solution comprising the specific substrate and a peroxide.

One of the more widely used peroxidases is horse radish peroxidase (HRP), for which a specific substrate is tetramethylbenzidine (TMB). HRP has found broad application as a marker enzyme in enzyme-immunological determination methods (enzyme immunoassays, EIA). A common feature of EIA systems is the exploitation of specific binding pair member interaction, such as an antigen-antibody interaction, for the determination of the presence or concentration of an analyte, e.g. antigen or antibody. A multitude of EIA systems have been described. These may be classified, for example, as systems with enzyme-labelled antigen and as systems with enzyme-labelled antibody.

One example of an EIA system with labelled antigen is the competitive solid phase EIA (enzyme linked immunosorbant assay, ELISA). In this system a known amount of an enzyme-labelled antigen and the antigen to be determined (analyte) compete for the limited number of binding sites of a specific antibody, which is immobilized on a solid phase. The higher the concentration of analyte, the lower the amount of enzyme-labelled antigen bound to the immobilized antibody. Making use of a calibration curve, the determination of the enzyme activity bound to the solid phase by interaction with the antibody allows the determination of the analyte concentration.

Another example is a labelled-antibody EIA which is a sandwich "assay" (or two site enzyme immunometric test). The assay includes two immunological reactions. In the first reaction a macromolecular antigen is bound more or less completely to an antibody immobilized on a solid phase. Next, the bound antigen is reacted with an excess of a conjugate consisting of a specific antibody and enzyme. The extent of the binding of the labelled antibody is proportional to the amount of antigen; thus, the determination of the remaining enzyme activity after removal of excess conjugate is a measure of the amount of antigen.

Another example of an EIA is a homogeneous enzyme immunoassay sold by Syva Company, Palo Alto, Calif. under the trade name EMIT. In EMIT assays the reaction takes place in one step in solution. Typically, the analyte from the test sample is combined with an enzyme-labelled analyte analog. Both the analyte and enzyme-labelled analyte analog are capable of competing for binding sites on an antibody for the analyte which is included in the reaction medium. By comparison with known standards, the enzyme activity that remains after the sample and other reagents are combined is a measure of the amount of analyte in the sample.

Thus, the determination of enzyme activity is an essential step in all EIAs. In general, enzyme activity is determined by well-known procedures. Typically changes of optical properties (absorption, fluorescence, luminescence) of an appropriate substrate effected by the enzymatic action is followed. Appropriate measuring instruments are used, and a linear proportionality between measuring signal and an amount of enzyme is advantageous.

Numerous chromogenic substrates for peroxidases, particularly horseradish peroxidase, have been reported. Many involve oxidation of a leuco dye to its colored form. Typical of this type of substrate is tetramethylbenzidine, 3,3 -bis-(3-carboxypropoxy)benzidine, N-ethyl- 3-aminocarbazol, guiacol, azo-bis-tetramethyl-benzimidazol sulfonic acid (ABTS), etc. In another class of substrates, the oxidized substrate forms a color by reacting with its own unoxidized form. Examples of such self-coupling includes p-hydroxyphenylpropionic acid, 4-chloronaphthol, and o-phenylenediamine. A related class of substrates, called "developers", are oxidized to intermediates that condense with color-forming molecules, called "couplers", to form dyes. Typical of this class of substrates are N-methylbenzothiazolone hydrazone and aminoantipyrene, either of which on oxidation can couple to electrophilic compounds such as aminobenzoic acid, diketones, phenols, etc.

The second class of substrates are of special interest because $HRP/H_2O_2$ catalyzes the condensation of two compounds. Ease of manipulation makes a dual substrate system attractive for various applications in EIA. For certain applications it is desirable for the system to involve a sensitive, precipitable, chromogenic substrate. One substrate which has been recently published by a group at Kodak is precipitable and has the capability of detecting <50 pg/mL of HRP in 30 minutes (D. J. Danner, et al., (1973) *Arch Biochem Biophys,* 156:759; P. E. Weller, et al. (1985) *Arch Blochem Biophys,* 243(2):633–643; European Patent 02527457; H. B. Dunford et al, (1986) *Arch BioChem Biophys,* 251(2):536–542; U.S. Pat. No. 4,089,747).

Benzidine and 3,3'-dimethoxybenzidine have been shown to oxidatively couple with 4-substituted or unsubstituted 2-t-butylphenols where the substituent is methoxy or halide (Josephy, et al., infra). In these reactions the substituent, or hydrogen when there was no substituent, was displaced by the nitrogen of an oxidized benzidine to form a merocyanine dye. However, there was no recognition of the use of this reaction for determination of peroxidase activity or hydrogen peroxide concentration or of its use in assays for analytes.

Also related to this class of substrates are p-hydroxy-and p-amino-, particularly p-dialkylamino-, anilines which, after oxidization, condense with couplers that produce a new chromophore and undergo bond cleavage leading to release a second dye. In these cases the coupler was a p-amino-or p-hydroxy-phenyl ether of a dye molecule, and the substrates were used to determine hydrogen peroxide concentrations. A large variety of this last type of substrate is described in EPO patent application 82101947.8. Again there was no recognition of whether or not these compounds were even useful for the determination of peroxidase activity.

2. Description of the Related Art

Josephy, et al. in *Carcinogenesis* (1982) 3 (10):1227–1230 describe the chemical structures of adducts formed by the oxidation of benzidine in the presence of phenols. Josephy, et al. in *Biochem, Pharmacol* (1984) 33 (7):1155–1156 describe the reaction of 4-substituted phenols with benzidine in a peroxidase system.

U.S. Pat. No. 4,853,328 describes a reagent for assaying hydrogen peroxide and a method of quantitative assay for hydrogen peroxide. European patent specification, publication No. 0060518 B1 describes a reagent for assaying hydrogen peroxide and a method of quantitative assay for hydrogen peroxide.

PCT International Application, Publication No. WO86/05207, discusses improvements relating to assay reagents, which are peroxidase-containing and tetramethyl-benzidine peroxidase-substrate reagents.

European Patent Application 0123902 A2 describes a procedure for the determination of peroxidase activity by end dilution titration and means for its realization. The procedure is carried out with a benzidine derivative in the presence of a non-chromogenic or low-chromogenic phenylene derivative, which is a proton donor, to retard color development for a sufficient period of time to permit a sharp dilution end point and thereafter detecting the peroxidase activity.

U.S. patent application Ser. No. 4,279,993 discloses an indicator composition and test device containing amine oxide and a method of its use. The composition contains a benzidine-type indicator.

Semi-quantitative determination of urine glucose with a carrier matrix containing glucose oxidase, a peroxidase and m-anisidine, optionally with tetramethylbenzidine is described in U.S. Pat. Nos. 4,391,905 and 4,391,906.

U.S. Pat. No. 4,556,640 discusses a stabilized test composition, device and method for the determination of peroxidately active substances.

Ionic compounds containing the cationic meriquinone of a benzidine are disclosed in U.S. Pat. No. 4,789,630.

European Patent Application, Publication No. 0060518 A1 discusses reagents for assay of hydrogen peroxide especially in diagnostic systems with a chemical moiety and fluorescing moiety present.

A test composition for peroxidately active substance with aniline derivative present as a stabilizer and device and method for the determination of peroxidatively active substances is disclosed in European Patent Application, Publication No. 0130520 A1.

Ethanol determination in aqueous samples with alcohol oxidase, peroxidase, and a reduced chromogenic indicator is described in European Patent Application, Publication No. 0164008 A2.

U.S. Pat. No. 4,587,220 discusses ascorbate interference-resistant composition, device and method for the determination of peroxidately active substances.

Quantitative determination of hemoglobin and cytochemicals staining for peroxidase using 3,3'-5,5'-tetramethylbenzidine dihydrochloride as a safe substitute for benzidine is described by H. H. Liem, et al. (1979) *Analytical Biochemistry* 98:388–393.

Europaische Patentanmeldung 0224210 A1 describes a color forming reagent for measuring peroxidase activity containing tetralkylbenzidine, peroxide and acidic buffer to improve sensitivity.

Stabilized enzyme substrate solutions are disclosed in PCT International Application, Publication No. WO 86/04610.

U.S. Pat. No. 4,503,143 discloses an enzyme immunoassay with two-parts solution of tetramethylbenzidine as chromogen.

A test composition for the detection of peroxidatively active substances is described in UK Patent Specification 1560077.

U.S. Pat. No. 3,527,331 discusses substantially anhydrous, solid assay materials for the determination of reagent for assaying aldolase. The materials are rendered storage stable by the presence of certain polyhydric compounds preferably manitol, sorbitol, lactose or polyvinyl alcohol. An indicator composition and test device containing amine oxide and a method of its use is disclosed in U.S. Pat. No. 4,279,993.

U.S. Pat. No. 4,310,626 discloses interference-resistant composition, device and method for determining a peroxidatively active substance in a test sample.

Stabilization of indicators for detecting enzyme activity is described in U.S. Pat. No. 4,615,972.

An assay for peroxidative enzyme activity is discussed in U.S. Pat. No. 4,596,770.

A specific binding assay employing an enzyme-clearable substrate as a label is disclosed in U.S. Pat. No. 4,279,992.

An agent for the determination of peroxidase activity, with stabilizer, is described in U.S. Pat. No. 4,891,314.

SUMMARY OF THE INVENTION

One embodiment of the present invention is a method for determining a peroxidatively active catalyst. The method comprises the step of detecting a substance formed by the coupling reaction of (a) the product of the peroxidatively active catalyst-catalyzed oxidation of a benzidine having at least one of its amine nitrogen atoms being primary and a hydrogen atom in a position ortho to this primary amine nitrogen with (b) a coupler other than the benzidine.

One aspect of the invention is directed to couplers having a group of the formula:

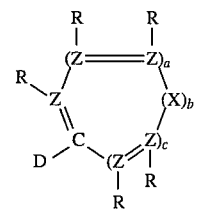

wherein:

$X$ is $O$, $S$, or $NR_1$ wherein $R_1$ is H, alkyl, or aryl, with the proviso that O or S be bound to carbon atoms;

$Z$ is C or N, preferably no more than three Z's are N, more preferably only one Z is N, most preferably Z is C;

$b$ is 0 or 1;

$a$ and $c$ are independently 0, 1 or 2 with the proviso that the ring contain 5 to 7 atoms, preferably 6 atoms;

R are independently H, halogen (Cl, Br, I, F), or a substitutent having from 1 to 50 atoms (other than the requisite hydrogen atoms necessary to satisfy the valencies of such atoms), which atoms are independently selected from the group consisting of carbon, oxygen, nitrogen, sulfur, phosphorus, or two R's can be taken together to form a ring, being substituted or unsubstituted, an unfused ring or part of a fused ring system, wherein one R is OH, SH, or amino nitrogen (including a ring amino nitrogen) bound to a site on the ring, such site being separated from D by an even number of ring atoms excluding X; and D is OH, halogen, $OR_2$, or $SR_2$ wherein $R_2$ together with O or S is a leaving group with the proviso that the two electron oxidation potential of 1 is greater than that of the benzidine. The ring in coupler 1 may be in the form of benzene, pyrrole, furan, thiophene, pyridine, imidazole, thiazole, pyrazine, pyrimidine, pyrazole, oxazole, isoxazole, pyridazine, azepine, and so forth.

Another aspect of the invention is directed to the above method wherein the product that couples with the coupler, namely, the oxidized benzidine, has the formula:

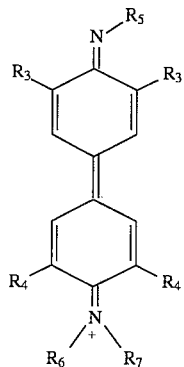   2 wherein
$R_5$ is H, $R_6$ and $R_7$ are independently a member selected from the group consisting of H, alkyl, alkoxy, aryl, and aralkyl, wherein carbon atoms of a member of the group bear independently H or one or more of the functionalities selected from the group consisting of olefins, acetylenes, ethers, thioethers, amines, carboxylic acids, sulfonic acids, phosphoric acids, ketones, aldehydes, nitriles, carboxamides, sulfonamides, carbamates, and ureas, and $R_3$ and $R_4$ are independently a member selected from the group consisting of H, F, Cl, Br, I, arylthio, alkylthio, aryloxy, alkyl, alkoxy, and aralkyl, wherein at least one of $R_3$ is H and carbon atoms of a member of the group bear independently H or one or more of the functionalities selected from the group consisting of olefins, acetylenes, ethers, thioethers, amines, carboxylic acids, sulfonic acids, phosphoric acids, ketones, aldehydes, nitriles, carboxamides, sulfonamides, carbamates, and ureas, or $R_6$ or $R_7$ may be taken together with $R_3$ or $R_4$, or $R_6$ may be taken together with $R_7$, to form one or more rings that are fused or unfused, saturated or unsaturated, or a combination thereof.

Another embodiment of the invention is a method for determination of peroxidase. A sample suspected of containing peroxidase is contacted with (a) a hydroperoxide, (b) a benzidine wherein at least one of the amine nitrogens of the benzidine is primary and the position on the aromatic ring ortho thereto bears a hydrogen atom, and (c) a coupler other than benzidine having a two electron oxidation potential greater than that of the benzidine. A product of the reaction of (a), (b), and (c) is detected by measurement of an electromagnetic signal.

Another embodiment of the invention is a method for determining a peroxidatively active catalyst where the method comprises:

(1) contacting a medium suspected of having a peroxidatively active catalyst with a hydroperoxide, a benzidine and a compound 3 of the formula

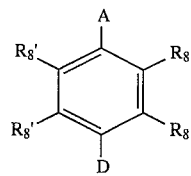   3 wherein:
$R_8$ and $R'_8$ are independently H, halogen or a substituent having from 1 to 50 atoms (other than the requisite hydrogen atoms necessary to satisfy the valencies of such atoms), which atoms are independently selected from the group consisting of carbon, oxygen, nitrogen, sulfur, phosporous, or two $R_8$s and/or $R'_8$s can be taken together to form a ring or rings being substituted or unsubstituted, a single ring or part of a fused ring system, and A is independently OH, $N(R_9)_2$ or SH, wherein $R_9$ is independently selected from the same group as $R_8$ other than halogen and is bonded to nitrogen at a saturated carbon atom or can be taken together with $R_8$ or $R'_8$ and/or with another $R_9$ to form a ring or rings being substituted or unsubstituted, a single ring or part of a fused ring system, D is halo, $OR_{10}$, or $SR_{10}$ wherein $R_{10}$ together with O or S is a leaving group wherein the linking functionality to $R_{10}$ can be an ether, thioether, ester (including S and P esters), urethane, carbonate, and so forth, inclusive of such O or S atoms, with the proviso that 3 cannot be substantially oxidized to a quinoid compound by the product of said catalyst-catalyzed oxidation of the benzidine, and (2) detecting a substance formed by reaction of said product with compound 3.

In one aspect of this embodiment the benzidine has the formula

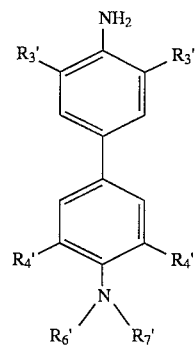   4 wherein:
$R'_6$, and $R'_7$ are independently selected from the group consisting of H, alkyl, alkoxy, aryl, and aralkyl wherein carbon atoms of a member of the group bear H or one or more of the functionalities selected from the group consisting of ethers, olefins, acetylenes, thioethers, amines, carboxylic acids, sulfonic acids, phosphoric acids, ketones, aldehydes, nitriles, carboxamides, sulfonamides, carbamates and ureas, and $R'_3$ and $R'_4$ are a member independently selected from the group consisting of H, F, Cl, Br, I, arylthio, alkylthio, aryloxy, alkyl, alkoxy, aryl and aralkyl wherein at least one of $R_3$ is H and carbon atoms of a member of the group bear H or one or more of the functionalities selected from the group consisting of ethers, olefins, acetylenes, thioethers, amines, carboxylic acids, sulfonic acids, phosphoric acids, ketones, aldehydes, nitriles, carboxamides, sulfonamides, carbamates and ureas, where $R'_6$ and $R'_7$ may be taken together with $R'_3$ or $R'_4$ or $R'_6$ may be taken together with $R'_7$ to form one or more rings that are fused or unfused, saturated or unsaturated or a combination thereof.

In another aspect of this embodiment the compound 3 has the formula

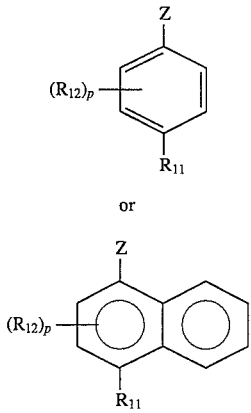

wherein:

P is 1 to 4;

Z is OH, $NH_2$, NH(lower alkyl) or N (lower alkyl)$_2$;

$R_{12}$ is lower alkyl, —COOR$_{13}$, —CN, —Cl, —Br, —I, —NO$_2$, —SO$_2$R$_{13}$, —PO$_3$(R$_{13}$)$_2$, —C(O)N(R$_{13}$)$_2$, —SO$_2$N(R$_{13}$)$_2$ wherein $R_{13}$ is independently H, alkyl, carboxyalkyl amino-substituted lower alkyl, N (lower alkyl)$_2$ or NH (lower alkyl)-amino-substituted lower alkyl; and $R_{11}$ is —OR$_{14}$ wherein $R_{14}$ is selected from the group consisting of H, alkyl or carboxyalkyl, —C(O)R$_{15}$, —C(O)N(R$_{16}$)R$_{16}$, —SO$_2$R$_{15}$, —SO$_3$R$_{16}$, P(OR$_{15}$)(OR$_{15}$), PO(OR$_{16}$)(OR$_{16}$) wherein $R_{15}$ is an organic group bound through a carbon atom and $R_{16}$ is independently selected from the group consisting of hydrogen and an organic group bound through a carbon atom, with the proviso that $R_{12}$ not be in a position ortho to Z when R12 is an electron-withdrawing group and Z is OH and that no more than one $R_{12}$ be an electron-withdrawing group.

Another embodiment of the invention is a method for detecting peroxidase activity wherein the method comprises:

(1) combining a medium suspected of having peroxidase activity with (1) a hydroperoxide, (2) a benzidine 6 of the formula

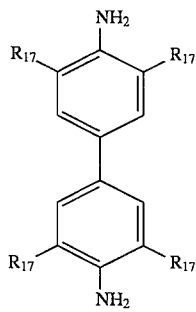

wherein $R_{17}$ is independently H, lower alkyl, lower alkoxy, or carboxy lower alkoxy and at least one $R_{17}$ is H, and (3) a compound 7 of the formula

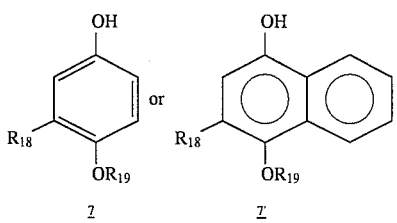

wherein:

$R_{19}$ is independently H, alkyl, aryl, or carboxyalkyl, $R_{18}$ is H, —COOR$_{19}$, —CN, —Cl, —Br, —I, —NO$_2$, —SOR$_{19}$—, —SO$_2$R$_{19}$—, —PO$_3$(R$_{19}$)$_2$, —C(O)N(R$_{19}$)$_2$, —SO$_2$N(R$_{19}$)$_2$, —C(O)NH(CH$_2$)$_q$N(R$_{20}$)$_2$, —C(O)NH(CH$_2$)$_q$NH(CH$_2$)$_s$N(R$_{20}$)$_2$, o

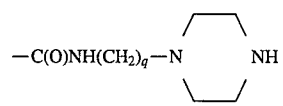

wherein $R_{20}$ is independently H or lower alkyl and wherein q is 1 to 10 and s is 1 to 10, and (2) detecting a substance formed by the reaction of the product of the peroxidase catalyzed oxidation of benzidine 6 with compound 7 or 7'.

Another embodiment of the present invention is a kit for detecting peroxidase activity. The kit comprises in packaged combination a benzidine as defined and a compound 3.

Another embodiment of the present invention is a kit for detecting peroxidase activity, which kit comprises: (1) a hydroperoxide, (2) a benzidine 6 and (3) a compound 7 or 7'.

Another embodiment of the invention concerns an improvement in a method for the determination of an analyte in a sample suspected of containing the analyte. The method comprises combining the analyte, or an agent probative of the analyte, with a peroxidatively active substance in a liquid medium and determining the effect of the analyte or the agent on the peroxidative activity of the substance. The improvement in the determining step comprises the step of detecting a substance associated with the coupling of the peroxidatively-active-substance-catalyzed oxidation product of a benzidine and a coupler other than the benzidine.

Another embodiment of the present invention concerns an assay for an analyte which is a member of a specific binding pair (sbp). The assay comprises combining a medium suspected of containing the analyte, or a second sbp member whose presence is related to the presence of the analyte, with a peroxidase enzyme conjugated to a third sbp member. One or more of the analyte and the sbp members can be analogs of, or complementary to, one another. Next, the activity of the peroxidase enzyme is determined by treating the peroxidase enzyme with a hydroperoxide, a benzidine wherein at least one amino group of the benzidine is primary and the position on the aromatic ring ortho thereto bears a hydrogen atom, and a coupler other than the benzidine wherein the coupler has a two electron oxidation potential greater than that of the benzidine.

DESCRIPTION OF THE SPECIFIC EMBODIMENTS

The present invention is directed to the detection of a peroxidatively active catalyst such as a peroxidase. In the method of the invention a sample is contacted with (a) a hydroperoxide, (b) a benzidine where at least one amine nitrogen of the benzidine is primary and at least one of the positions on the aromatic ring ortho to that amine group bears a hydrogen atom substituent, and (c) a coupler other than the benzidine having a two electron oxidation potential greater than that of the benzidine. The product of the reaction of the above reaction components is detected by measurement of a signal, including without limitation absorbance, fluorescence, chemiluminescence, potentiometric, turbidometric, etc. Generally, except for the above requirements for benzidine, the benzidine may be unsubstituted or substituted in other positions with the proviso that substantial planarity of the benzidine system must be maintained to allow oxidation to occur and the oxidation potential must be sufficiently low to permit oxidation by the hydroperoxide. The coupler may be any compound which will enter into a coupling reaction with the oxidized form of the benzidine to yield a detectable product, which can be a coupled product or a product derived from a leaving group on the coupler, which leaving group is cleaved from the coupler during or after the coupling reaction.

The present invention is based on the observation that certain benzidines oxidized with a peroxidatively active catalyst, such as horseradish peroxidase, and a hydroperoxide enter into coupling reactions with certain phenols and anilines that are para-substituted with leaving groups. One preferred leaving group is hydroxyl, which has not previously been shown to be displaced in either a chemical or enzymatically induced coupling reaction. Other leaving groups of this invention may, but need not be, active leaving groups, that is, when they are released they provide some detectible change or initiate some additional reaction. Usually, they are chromophoric.

All of the present reactions with benezidines are very much more rapid than the reaction of such couplers with other developers, such as N,N-dimethylphenylenediamine and N,N-diethyl-3-chloro-p-phenylene diamine, and they, therefore, provide greater sensitivity of detection of peroxidase activity. The sensitivity enhancement achieved in the present invention is at least 20 fold greater than the sensitivity achieved in other systems such as N,N-dimethylphenylenediamine with gentisic acid.

The present invention provides a method for very rapid catalytic cleavage of otherwise very stable bonds with the formation of a detectable product. The method permits detection of peroxidatively active catalysts, such as peroxidases, with very great sensitivity by means of a class of substrates which can be soluble and yet which, when desired, can yield highly colored insoluble products. These products can, for example, be caused to deposit on a support at a site where a peroxidase is localized as a result of the binding reaction in an immunoassay and thus provide a means for highly sensitive detection of antigenic analytes. Additionally, the invention provides a way to release covalently bound groups under very mild conditions such as the release of a fluorogenic, chromogenic or chemiluminescent group.

In the present invention unsubstituted and substituted benzidines (as defined) are oxidized with a peroxidase and a hydroperoxide in the presence of any of a large variety of phenol and aniline couplers that are para-substituted with a hydroxy, halogen, carbamoyloxy acyloxy, or aryloxy group. A water solubilizing group may also be present, either bound to a leaving group or to the aromatic ring of the phenol or aniline. The products are exceptionally highly colored and can be manipulated to be soluble or insoluble depending on the substituents of the coupler and/or the benzidine. Exemplary of water-solubility imparting functionalities are sulfate, sulfite, phosphate, phosphite, and so forth. Exemplary of water insolubility imparting groups are hydrophobic groups such as alkyl, acyl, etc.

For example, to obtain a more precipitable product oppositely charged species for the benzidine and the coupler can be chosen. After reaction, a merocyanine dye forms having all charges neutralized. The precipitation of this dye is thus enhanced. For example, the substituents in the 3 and 3'-positions of the benzidine can contain negative charges and a substituent of the coupler can contain a corresponding number of positive charges. The resulting coupled product is neutral.

Alternately, the benzidine may have no charged substituents and the coupler may have a hydrophobic substituent that would render it insoluble but for the presence of a charged leaving group. On coupling, the leaving group is lost and the resulting hydrophobic product is no longer soluble.

Before proceeding further with the description of the specific embodiments of the present invention, a number of terms will be defined.

Oxidation of benzidine—refers to the abstraction of two electrons and one or two protons, from a benzidine. The oxidation normally is produced by a hydroperoxide oxidant but could, for example, be produced by electrochemically oxidizing the catalyst. The oxidant is usually hydrogen peroxide, perborate, or an alkyl or acylhydroperoxide. Hydrogen peroxide can be added as a reagent or can be generated in situ, by, for example, reaction of glucose and oxygen with glucose oxidase. The product is a benzidine quinone imine which may be electrically neutral or be singly or doubly protonated depending on the acidity of the medium.

Hydroperoxide—an oxidant, refers to any compound containing the hydroperoxide (—O—H) group. Examples of hydroperoxides include both organic and inorganic hydroperoxides, e.g., hydrogen peroxide, urea hydrogen peroxide, peracids, and perborate.

Organic hydroperoxides contemplated for use in the invention can be selected from many well known organic hydroperoxides. Among hydroperoxides which are particularly suitable are methyl hydroperoxide, ethylhydroperoxide, cumeme hydroperoxide, t-butyl hydroperoxide, diisopropylbenzene hydroperoxide, 2,5-dimethylhexane-2,5-dihydroperoxide, paramenthane hydroperoxide, and other well-known hydroperoxides, which are suitable for oxidizing the benzidine used, or mixtures of these compounds.

Peroxidatively active catalyst—refers to an oxidation catalyst which catalyzes reduction of a hydroperoxide by an electron donating agent, particularly benzidine. Subclasses of peroxidative catalysts include aquated or otherwise complexed transition metal ions which are reactive toward electron transfer (e.g., copper, iron, cobalt, maganese), hemes, hemoproteins, and specific enzymes known as peroxidases such as lactoperoxidase. A subclass of peroxidases, the "haloperoxidases", employ halide ion as a cofactor. The most commonly used peroxidase is purified from horseradish roots and is designated horseradish peroxidase or HRP.

Benzidine—a 4,4'-diaminobiphenyl; for purposes of the present invention at least one of the amino groups of the benzidine is primary and the position on the aromatic ring ortho to such amino group bears a hydrogen atom substituent. To exemplify this distinction benzidine and 3,3'-dimethylbenzidine function in the present invention, whereas 3,3',5,5'-tetramethylbenzidine and N,N,N',N'-tetramethylbenzidine do not react at a rate acceptable for assays. The remaining positions on the amino groups of the benzidine may contain substantially electroneutral substituents such as aryl, alkyl, H, or alkoxy, but not carbonyl, sulfonate or other electron withdrawing groups, that is, anything that causes too large an increase in the oxidation potential and inactivates the benzidine to oxidation. The remaining positions on the aromatic ring may include in addition weakly electron withdrawing groups such as halogen, acylamido, phosphates, etc, again the primary requirement that the oxidation of the benzidine not be inhibited. Further, the additional substituents may contain additional ring systems, as long as substantial planarity of the molecule is maintained so that oxidation of the benzidine in accordance with the present invention may be achieved.

In one aspect the benzidine has the formula

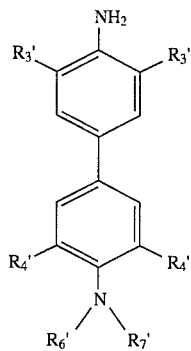

4 wherein:

$R'_6$, and $R'_7$ are independently selected from the group consisting of H, alkyl, alkoxy, aryl, and aralkyl wherein carbon atoms of a member of said group bear H or one or more of the functionalities selected from the group consisting of ethers, olefins, acetylenes, thioethers, amines, carboxylic acids, sulfonic acids, phosphoric acids, ketones, aldehydes, nitriles, carboxamides, sulfonamides, carbamates and ureas, and $R'_3$ and $R'_4$ are a member independently selected from the group consisting of H, F, Cl, Br, I, arylthio, alkylthio, aryloxy, alkyl, alkoxy, aryl, aralkyl, and aralkoxy wherein at least one of $R'_3$ is H and carbon atoms of a member of said group bear H or one or more of the functionalities selected from the group consisting of ethers, olefins, acetylenes, thioethers, amines, carboxylic acids, sulfonic acids, phosphoric acids, ketones, aldehydes, nitriles, carboxamides, sulfonamides, carbamates and ureas, where $R'_6$ and $R'_7$ may be taken together with $R'_3$ or $R'_4$, or $R_6$ may be taken together with $R'_7$, to form one or more rings that are fused (e.g., naphthyl, anthracyl, etc.), or unfused (e.g., biphenyl, etc.), saturated (e.g., aromatic or aryl), or unsaturated (e.g., cycloalkyl, etc.), or a combination thereof (e.g., cycloalkyl containing one or more olefin bonds).

In another aspect the benzidine has the formula

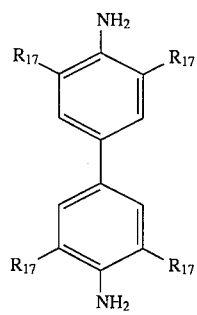

6 wherein $R_{17}$ is independently H, lower alkyl, lower alkoxy, or carboxy lower alkoxy, and at least one $R_{17}$ is H.

Exemplary benzidines are

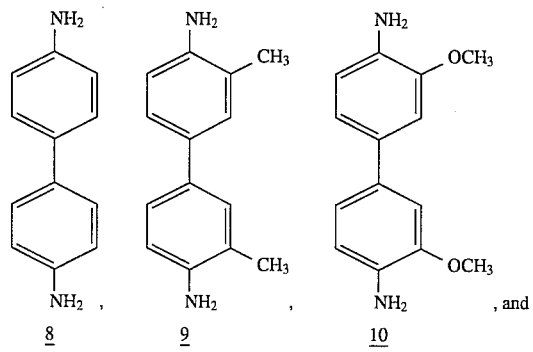

8, 9, 10, and

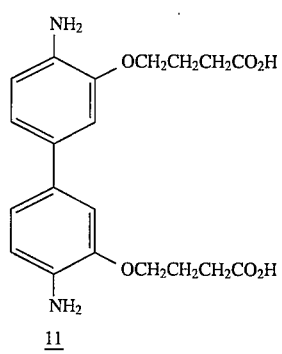

11

Benzidines that can be utilized in the present invention are generally known, commercially available or can be synthesized according to procedures well known to those skilled in the art.

Alkyl—a monovalent branched or unbranched radical derived from an aliphatic hydrocarbon by removal of one H atom; includes both lower alkyl and upper alkyl.

Lower alkyl—alkyl containing from 1 to 5 carbon atoms such as, e.g., methyl, ethyl, propyl, butyl, isopropyl, isobutyl, pentyl, isopentyl, etc.

Upper alkyl—alkyl containing more than 6 carbon atoms, usually 6 to 20 carbon atoms, such as, e.g., hexyl, heptyl, octyl, etc.

Aryl—an organic radical derived from an aromatic hydrocarbon by the removal of one atom and containing one or more aromatic rings, usually one to four aromatic rings, such as, e.g., phenyl (from benzene), naphthyl (from naphthalene), etc.

Aralkyl—an organic radical having an alkyl group to which is attached an aryl group, e.g., benzyl, phenethyl, 3-phenylpropyl, 1-naphthylethyl, etc.

Alkoxy—an alkyl radical attached to the remainder of a molecule by an oxygen atom, e.g., methoxy, ethoxy, etc.

Aryloxy—an aryl radical attached to the remainder of a molecule by an oxygen atom, e.g., phenoxy, naphthoxy, etc.

Aralkoxy—an aralkyl radical attached to the remainder of a molecule by an oxygen atom, e.g., benzoxy, 1-naphthylethoxy, etc.

Fused ring—a polycylic compound in which at least two rings have two atoms in common, e.g., naphthalene, anthracene, etc.

Unfused (or single ring)—a compound having one or more rings none of which have two atoms in common, e.g., benzene, biphenyl, etc.

Substituted—means that a hydrogen atom of a molecule has been replaced by another atom, which may be a single atom such as a halogen, etc., or part of a group of atoms forming a functionality such as a substituent having from 1 to 50 atoms (other than the requisite hydrogen atoms necessary to satisfy the valencies of such atoms), which atoms are independently selected from the group consisting of carbons, oxygen, nitrogen, sulfur, and phosphorus.

Alkylthio—an alkyl radical attached to the remainder of a molecule by a sulfur atom, e.g., methylthio, ethylthio, etc.

Arylthio—an aryl radical attached to the remainder of a molecule by a sulfur atom, e.g., phenylthio, naphthylthio, etc.

Electron-withdrawing group—a substituent which when bound to a molecule is capable of polarizing the molecule such that the electron-withdrawing group becomes electron rich and negatively charged. Such group is electron attracting and may be, by way of illustration and not limitation, halogen (Cl, Br, I, F), $NO_2$, CN, $CONR''_2$, $NR''^+$, $COOR''$, $-SO_3R''$, $-SO_2R''$, $-PO_3R''_2$, $-COR''$ wherein $R''$ is hydrogen, alkyl, or aryl, and the like.

Quinoid compound—paraquinoid; the chromophoric group

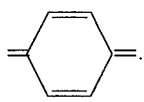

A substituent having from 1 to 50 atoms (other than the requisite hydrogen atoms necessary to satisfy the valencies of such atoms), which atoms are independently selected from the group consisting of carbon, oxygen, nitrogen, sulfur, and phosphorus—an organic radical; the organic radical has 1 to 50 atoms other than the requisite number of hydrogen atoms necessary to satisfy the valencies of the atoms in the radical. Generally, the predominant atom is carbon (C) but may also be oxygen (O), nitrogen (N), sulfur (S), phosphorus (P), wherein the O, N, S, or P, if present, are normally bound to at least a carbon atom and may be bound to one or more of each other or to hydrogen to form various functional groups, such as, for example, carboxylic acids, alcohols, thiols, carboxamides, carbamates, carboxylic acid esters, sulfonic acids, sulfonic acid esters, phosphoric acids, phosphoric acid esters, ureas, carbamates, phosphoramides, sulfonamides, ethers, sulfides, thioethers, olefins, acetylenes, amines, ketones, aldehydes, nitriles, and the like. Illustrative of such organic radicals or groups, by way of illustration and not limitation, are alkyl, aryl, aralkyl, and alkyl, aryl, and aralkyl substituted with one or more of the aforementioned functionalities; and fluorescer organic groups such as coumarins, xanthenes, squaraines, umbelliferones, fluoresceins, bimanes, merocyanines, naphthylamines, cyanines, luminols, acridinium esters, luciferin oxalate esters, all of which may also contain one or more of the aforementioned functionalities.

Leaving group—a substituent on the coupler that is capable of being cleaved therefrom during the condensation of the coupler with an oxidized benzidine. Generally, the leaving group is OH, a halogen (Cl, Br, I, F) atom or has an O or S atom bound to the coupler and further bound through a 0 to 1 carbon atom chain to an atom of an organic radical.

Particularly preferred leaving group substituents include, OH, $OCH_3$, $OCH_2COOH$, $OCH_2OCH_2CH_2COOH$, and chromogenic derivatives such as

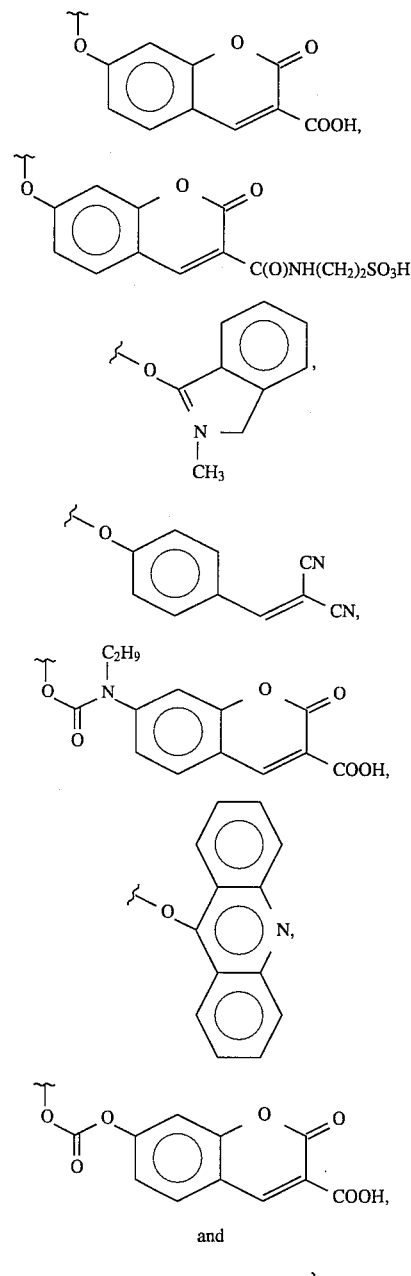

and

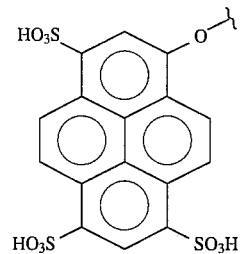

Other para leaving group substituents useful in this invention include those in EPO application 82102947.8 referred to hereinabove.

Coupler other than benzidine—an aromatic or heteroaromatic compound capable of coupling with an oxidized benzidine having 1 to 5 fused rings wherein a leaving group is bound to an aromatic ring in conjunction with a hydroxyl, sulfhydryl or amino group and having the ability to yield a signal upon reaction in accordance with the present invention. Compounds satisfying the above criteria can be employed as a coupler in the present invention. Generally, the coupler has a two electron oxidation potential greater than the benzidine; that is, it is unable to reduce oxidized benzidine to benzidene.

Two electron oxidation potential—is based on the ability of the coupler to give up two electrons and lose zero to two protons depending on the acidity of the medium. The two electron oxidation potential can be determined in a standard electrochemical cell using a reference electrode such as a hydrogen, calomel, or Ag/AgCl electrode usually using a dropping mercury working electrode. The pH of the solution of coupler and benzidene will be adjusted prior to measurement to the same value as used in the desired coupling reaction. Alternatively, it can be observed directly whether the benzidine quinoneimine can be reduced to benzidine by the coupler by combining the two compounds in a solution and observing the disappearance of color of the quinoneimine and reappearance of benzidine which may be detected spectroscopically or by chromatography.

As mentioned above, the coupler should not be able to reduce the oxidized benzidine to benzidine. The oxidation potential of the coupler must be carefully selected to match the benzidine that is being used.

The coupler should be able to yield a detectible signal upon a condensation reaction with an oxidized benzidine in accordance with the present invention. The signal may be, for example, absorbance, fluorescence, chemiluminescence or detection of a precipitated product by, for example, gravimetric means. The fluorescence can be produced by excitation of a compound such as a coumarin, xanthene, squaraine, or umbelliferone, fluorescein, bimane, merocyanine dyes, naphthylamine, cyanines, luminol, acridinium esters, luciferin oxalate esters, and so forth. The reaction between an oxidized benzidine and a coupler can release a chromophoTe or other detectible group or can form a condensation product that is detectible, for example, by chemiluminescence, fluorescence, absorbance, precipitation, etc.

Couplers that may be used in the present invention are among couplers described in U.S. Pat. No. 4,853,328, the disclosure of which is incorporated herein by reference. Only those couplers may be used, of course, that would satisfy the above criteria.

In one aspect of the invention the couplers have a group having the formula:

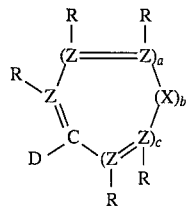

wherein:

X is O, S, or $NR_1$ wherein $R_1$=alkyl, H or aryl with the proviso that O or S be bound to C atoms, Z is C or N, b is 0 or 1, a, and c are 0, 1, or 2 with the proviso that the ring will contain 5 to 7 atoms.

R are independently H, halogen, or a substitutent having from 1 to 50 atoms other than the requisite hydrogen atoms necessary to satisfy the valencies of such atoms, which atoms are independently selected from the group consisting of carbon, oxygen, nitrogen, sulfur, phosphorus, or two Rs can be taken together to form a ring, being substituted or unsubstituted, a single ring or part of a fused ring system; such substituent can be an electron-withdrawing group as defined herein, an organic group as defined herein, or an organic group bound to I through an O or S atom; wherein a group selected from OH, SH and amino nitrogen (including a ring amino nitrogen) is bound to a site separated from D by an even number of ring atoms that do not include X; and D is OH, halogen, $OR_2$, or $SR_2$ wherein $R_2$ together with O or S is a leaving group as defined herein with the proviso that the coupler is substantially incapable of reducing the two electron oxidation product of the benzidine back to the benzidine. As a result, the coupler enters into a condensation reaction with the product.

In another embodiment of the invention the couplers are a compound 3 of the formula

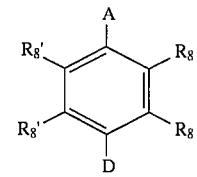

wherein:

$R_8$ and $R'_8$ are independently H, halogen or a substituent having from 1 to 50 atoms other than the requisite hydrogen atoms necessary to satisfy the valencies of such atoms, which atoms are independently selected from the group consisting of carbon, oxygen, nitrogen, sulfur, phosporous, halogen or two $R_8$s and/or two $R'_8$s can be taken together to form a ring or rings being substituted or unsubstituted, a single ring or part of a fused ring system; such substituent can be an electron-withdrawing group as defined herein, an organic group as defined herein, or an organic group bound to III through an O or S atom; and A is independently OH, $N(R_9)_2$ or SH, wherein $R_9$ is independently selected from the same group as $R_8$ other than halogen and is bonded to nitrogen at a saturated carbon atom or can be taken together with $R_8$ or $R'_8$ and/or with another $R_9$ to form a ring or rings being substituted or unsubstituted, a single ring or part of a fused ring system, D is halogen, $OR_{10}$, or $SR_{10}$ wherein $R_{10}$ together with O or S is a leaving group with the proviso that 3 cannot be substantially oxidized (i.e., the level of oxidation should be sufficiently low so that the predominant product will be 3 coupled to benzidine) to a quinoid compound by the product of the catalyst-catalyzed oxidation of the benzidine.

In another aspect of this invention the couplers are selected from compound 5 or 5' of the formula

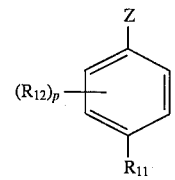

-continued or

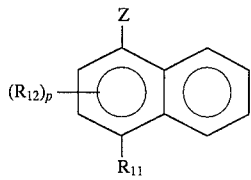

wherein:

p is 1 to 4;

Z is OH, $NH_2$, NH(lower alkyl) or N(lower alkyl)$_2$;

$R_{12}$ is lower alkyl, —$COOR_{13}$, —CN, —Cl, —Br, —I, —$NO_2$, —$SO_2R_{13}$, —$PO_3(R_{13})_2$, —$C(O)N(R_{13})_2$, —$SO_2N(R_{13})_2$ wherein $R_{13}$ is independently H, alkyl, carboxyalkyl, amino-substituted lower alkyl, N(lower alkyl)$_2$ or NH(lower alkyl)-amino-substituted lower alkyl; and $R_{11}$ is —$OR_{14}$ wherein $R_{14}$ is selected from the group consisting of H,alkyl or carboxyalkyl, —$C(O)R_{15}$, —$C(O)N(R_{16})R_{16}$, —$SO_2R_{15}$, —$SO_3R_{16}$, $P(OR_{15})(OR_{15})$, $PO(OR_{16})(OR_{16})$ wherein $R_{15}$ is an organic group bound through a carbon atom and $R_{16}$ is independently selected from the group consisting of hydrogen and an organic group bound through a carbon atom, with the proviso that $R_{12}$ not be in a position ortho to Z when $R_{12}$ is an electron-withdrawing group and Z is OH and that no more than one $R_{12}$ be an electron-withdrawing group.

In another aspect of the invention the coupler is a compound 7 or 7' of the formula

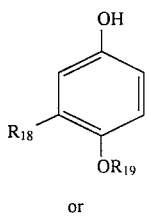

or

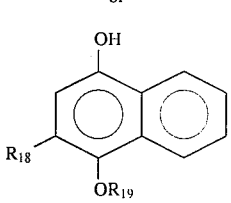

wherein:

$R_{19}$ is independently H, alkyl, aryl, carboxyalkyl, $R_{18}$ is H, —$COOR_{19}$, —CN, —Cl, —Br, —I, —$NO_2$, —$SOR_{19}$—, —$SO_2R_{19}$—, —$PO_3(R_{19})_2$, —$C(O)N(R_{19})_2$, —$SO_2N(R_{19})_2$, —$C(O)NH(CH_2)_qN(R_{20})_2$ —$C(O)NH(CH_2)_qNH(CH_2)_sN(R_2O)_2$ or

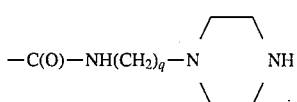

wherein $R_{20}$ is H or lower alkyl and wherein q is independently 1 to 10 and s is 1 to 10.

In another aspect of the invention the coupler is a compound selected from the group consisting of

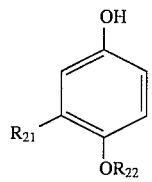

and

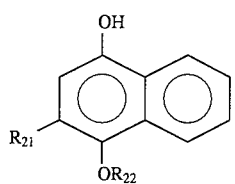

wherein $R_{21}$ is H, CN, Cl, or $C(O)R_{23}$ wherein $R_{23}$ is OH, lower alkyl, lower alkoxy, $NH_2$, lower alkylamino, —$NH(CH_2)_2NH(CH_2)_2NH_2$, $NH(CH_2)_2N(CH_3)_2$, or

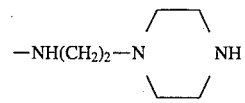

and $R_{22}$ is H, lower alkyl, or carboxy lower alkoxy; and

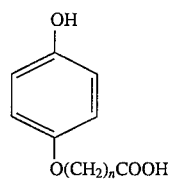

and

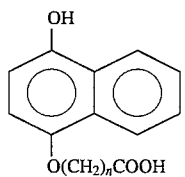

wherein n is 1 to 10; and

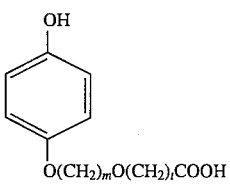

wherein m is 1 to 10 and t is 1 to 10; and

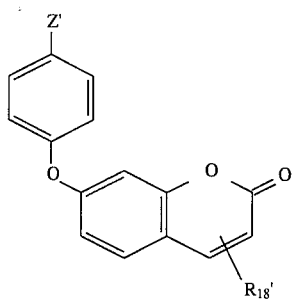

wherein Z' is OH or $N(R'_{19})_2$ and $R'_{18}$ is H, alkyl, aryl, or —C(O)X wherein X is $OR'_{19}$ or $N(R'_{19})_2$, and $R'_{19}$ is independently selected from H, lower alkyl, or lower alkyl substituted with —COOH, —SO$_3$H or —PO$_3$H; and

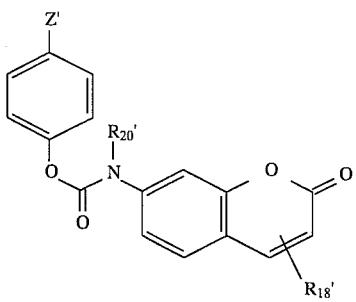

16 wherein R'$_{18}$ is defined above and R'$_{20}$ is H or lower alkyl.

Preferred couplers have hydrophilic, usually charged groups that provide water solubility. The products formed on condensation have solubility properties that depend on the substituents. Because two compounds condense in the reaction, substituents can be selected that impart good water solubility to each of the reactants but still provide for an insoluble condensation product. For example, by including a positive charge on the phenol coupler and a negative charge on the benzidine the product will be a zwitterion which will usually be less soluble than either component. Also, carboxylic acid groups on each compound can lead to a poorly soluble condensation product because the acidity of one of the carboxyls in the product will usually be lowered and, at the normal pH of the reaction of about 4–6, protonation and charge neutralization can therefore occur. Examples of phenols that yield insoluble products with dicarboxidine and 3,3'-dimethylbenzidine include 17, 18, 19, 24, 26, 32, 33, 34, and 58.

The couplers may have substituents other than the leaving group on the aromatic ring. The ring may be fused to other rings, for example, as in 4-chloronaphthol. Also electron donating, electron-withdrawing, or relatively electroneutral substituents can be present. Typical of substituents that have been used are mono-, di-, and tetra-methyl, methoxy, chloro, cyano, carboxy, carboxamido, 3-aminopropylcarboxamide, and carboethoxy. Additional hydroxyl and amino substituents are not desriable. In general, when the coupler is a phenol which can be oxidized to a quinone or quinoneimine, it is necessary to include an electron-withdrawing substituent attached to the aromatic ring such as halo, carboxy, nitro, or cyano. Without such a substituent the coupler is oxidized by two electrons by the oxidized benzidine thereby fully reducing the latter to the starting benzidine and preventing the coupling reaction. However, in general, for all couplers the coupling reaction can only take place if the coupler can be oxidized by the oxidized benzidine; but only a one electron oxidation to reduce the oxidized benzidine to a semiquinone can occur. Thus, when the coupler is a phenol with a para leaving group substituent there will usually be no electron-withdrawing substituent ortho to the phenolic hydroxyl group in order to permit the oxidized benzidine to oxidize the coupler. For a similar reason, it is usually not desirable to include a multiplicity of strong electron-withdrawing substituents in any of the couplers as these groups will increase the oxidation potential and slow the reaction.

Preferred couplers of the invention form products with extinction coefficients of at least 10,000 M$^{-1}$ cm$^{-1}$, preferably at least 20,000 and are formed in a yield in excess of 50%, preferably over 90% of the oxidized benzidine, at least during the first observable formation of the colored product. Compounds of the type 12 are particularly useful, especially gentisic acid (R$_{21}$=COOH, R$_{20}$=OH).

Particularly preferred couplers are:

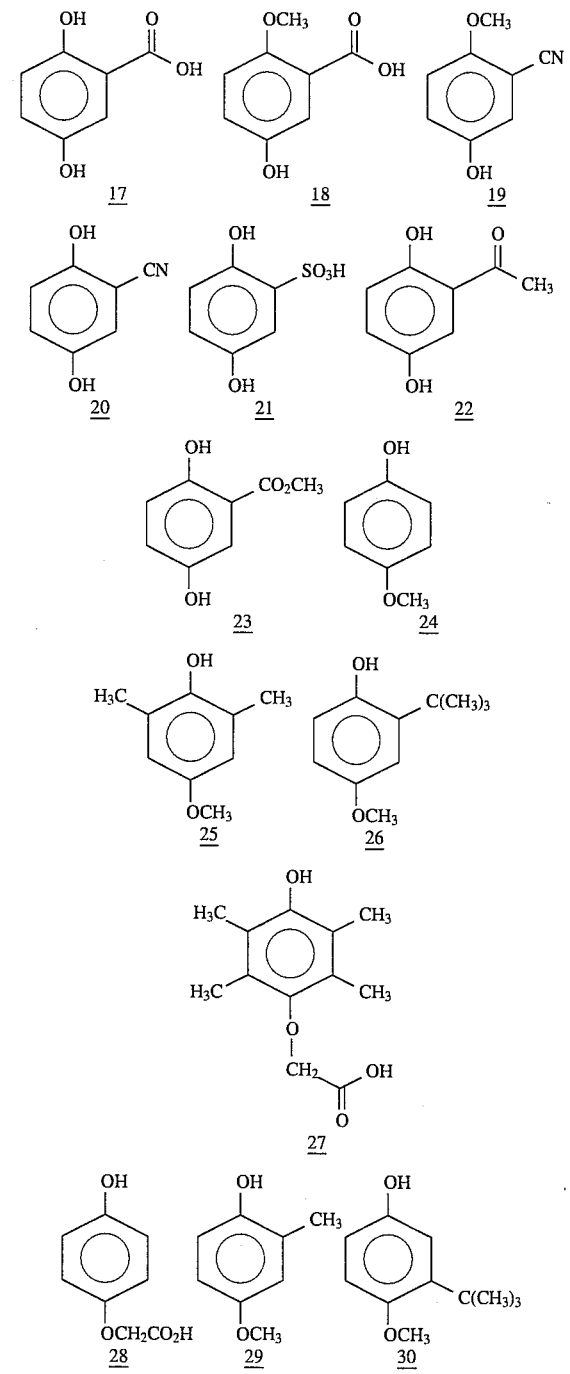

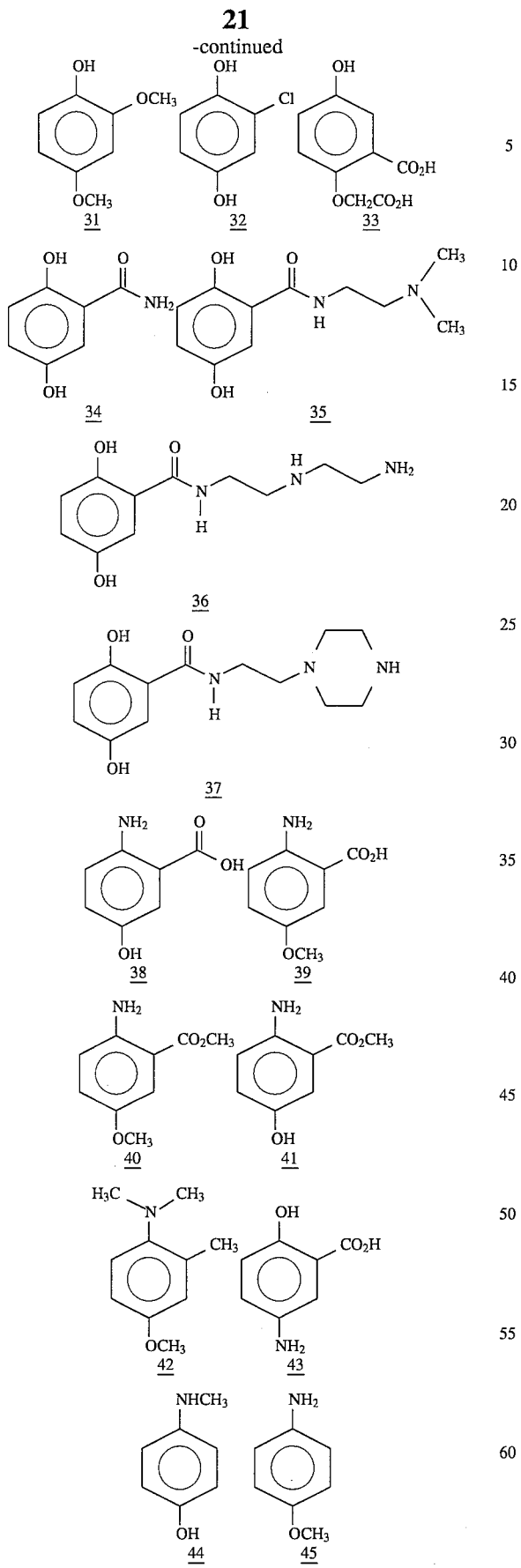
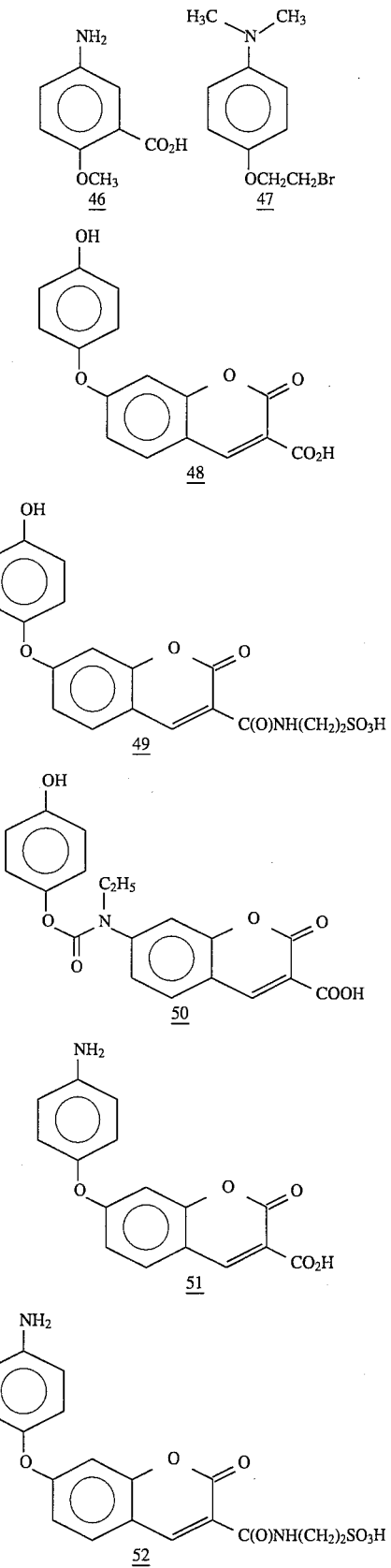

23
-continued

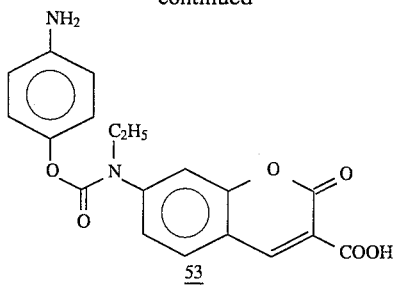
53

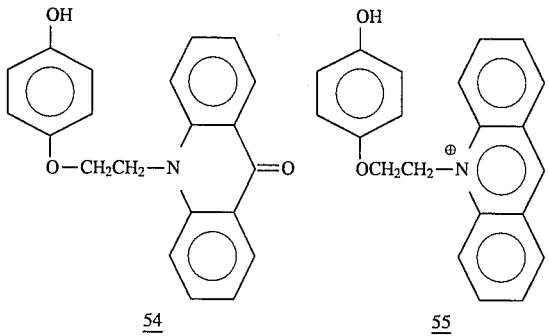
54  55

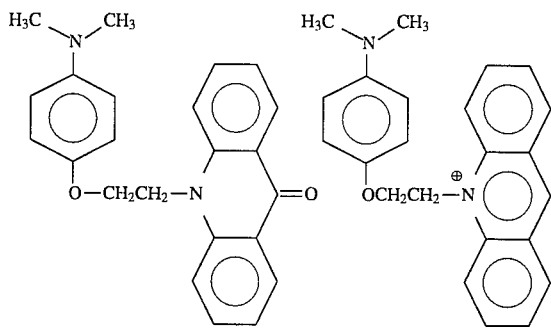
56  57

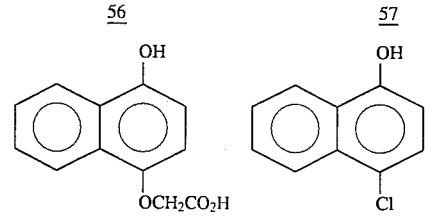
58  59

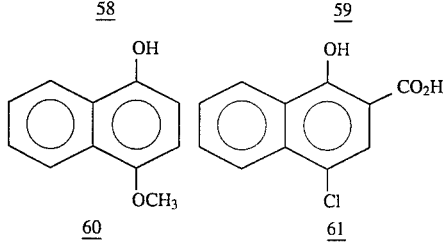
60  61

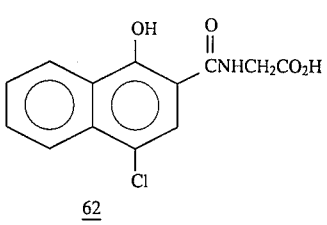
62

24
-continued

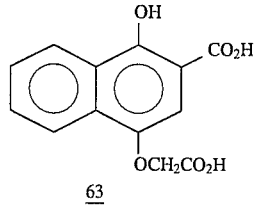
63

Factors which are relevant in determining the efficiency of the coupler include, first, the inability of the coupler to reduce the oxidized benzidine to benzidine as determined directly or by separate measurement of the two-electron redox potentials of the benzidine and coupler. If the potential of the coupler exceeds that of the benzidine under the experimental conditions of coupling, then reduction of the oxidized benzidine should not occur. Second, it is believed that an effective coupler will usually be able to undergo one electron oxidation by the oxidized benzidine and the latter must be reduced by one electron to produce a benzidene semiquinone. Although it is in principle possible to demonstrate by electrochemical methods, such as cyclic voltammetry, that the two half reactions should occur, it is in practice simpler to test directly whether the coupling reaction will occur. Thus, the presence of a reaction is taken as positive evidence for the one electron redox reaction. Third, there must be a leaving group para to the aryl amine or phenol of the coupler. Fourth, the concentration of the coupler must be sufficient to assure that the oxidized benzidine will react with the coupler without excessive loss due to reaction with unreacted benzidine remaining in the solution.

The selection of efficient couplers, therefore, depends on the benzidine that is used and on selecting compounds that can easily donate only one electron and that have a good leaving group. Usually, the leaving group will be at a strongly nucleophilic center, that is, a center of high electron density in the coupler, which is para to an electron donating group. The atom of the leaving group bound to this center will usually have a pair of electrons in a non-bonding orbital. The more electronegative the leaving group, the more electron donating the other substituents will have to be in order to provide a nucleophilic center to permit reaction with the oxidized benzidine.

For example, when dicarboxidine is the benzidine, if the leaving group is Cl which is quite electronegative, the following compounds are not useful couplers despite the presence of a para electron donating group:

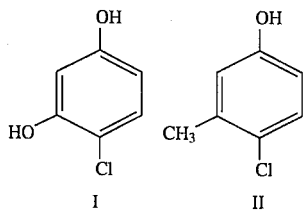
I  II but the following compounds are couplers:

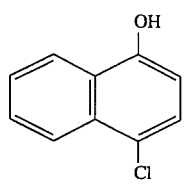
57

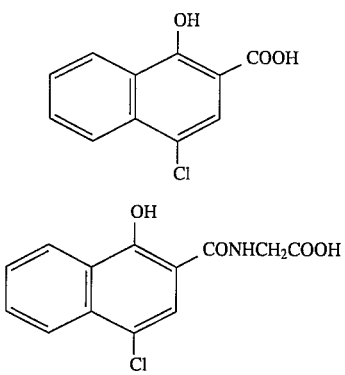

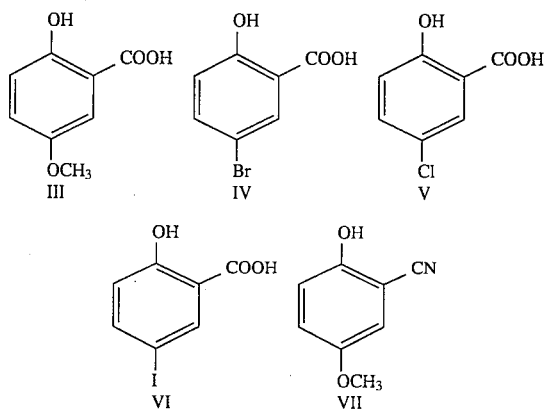

The ability of the latter group to act as couplers can be attributed to the greater nucleophilicity of the naphthalene nucleus at the low PH (4–6) of the couplers reaction.

Similarly, the following phenols are not couplers when using dicarboxidine:

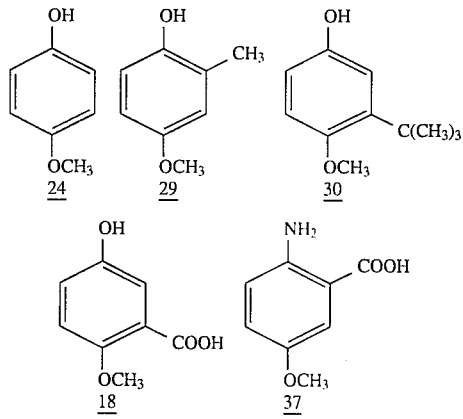

whereas the following compounds are couplers:

In this case, the latter group is oxidized by one electron followed by the ready loss of a proton to produce a radical which can couple with the benzidine semiquinone in the case of the phenols, whereas in the former group the radical that is formed following loss of an electron and a proton is stabilized by the ortho substituent and cannot readily couple. By contrast, in the latter group, there is either no stabilizing substituent or, when present, it is in a less stabilizing meta position. In the case of the highly electron rich amino group, nucleophilic substitution may occur directly or by initial electron transfer without proton loss.

In still another set of examples, the following compounds are not couplers because they can be oxidized to quinones by the oxidized dicarboxidine. That is, the phenols have a lower two-electron redox potential than dicarboxidine:

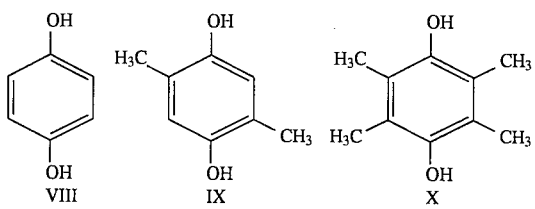

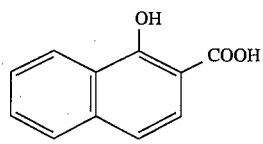

whereas the following hydroquinones that are less readily oxidized are couplers:

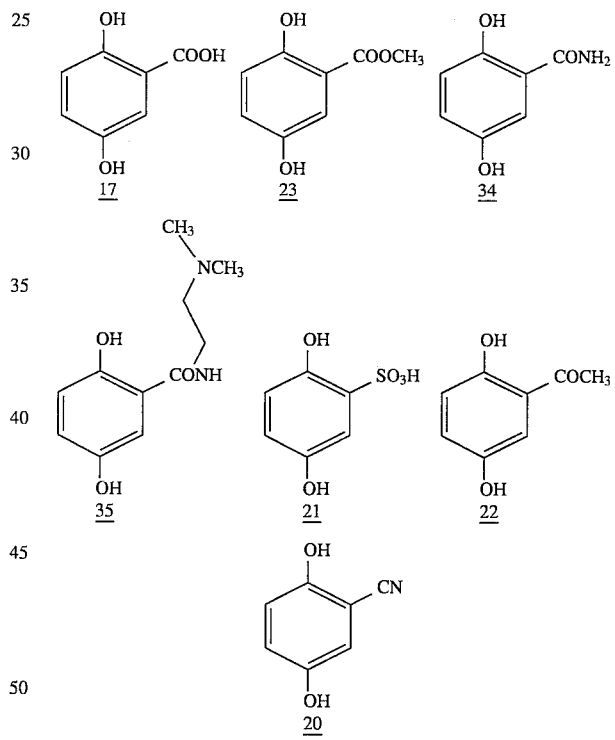

This latter group can also be compared with an additional group of hydroquinones that are not couplers because their redox potential is so high that they are not oxidized by oxidized dicarboxidine and/or they are insufficiently nucleophilic.

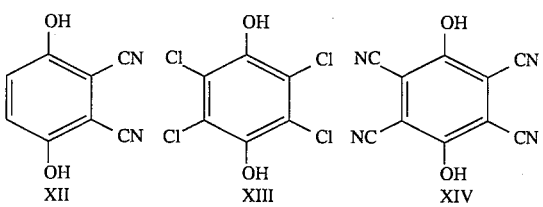

In general, it has been found that hydroquinones whose corresponding quinones have cathodic polarographic half wave potential (relative to the standard calomel electrode or SCE) greater than 0.58 volts are not couplers with dicarboxidine because they are oxidized by oxidized dicarboxidine. When the quinone has a half wave potential between 0.10 and 0.54 volts the corresponding hydroquinone is a coupler. When the quinone has a half wave potential below 0.1 volt the hydroquinone cannot be oxidized and it again is not a coupler. See Oldfield, et al., *J. Physical and Colloid Chem.* (1951) 1255 and "Oxidation-Reduction Potentials or Organic Systems" ed. W. M. Clark, chapter 4, page 737 (J. Q. Chambers) published by Williamp and Wilkins, Baltimore (1960).

Couplers that can be utilized in the present invention include known compounds that are commercially available and/or can be synthesized by procedures known in the art. Exemplary of various substituted phenols and anilines that have been prepared and their general method of preparation are as follows:

25: Catalytic reduction of 2,6-dimethyl quinone with $H_2,^{Pd}/C$ in ethanol gave the hydroquinone, which in turn was methylated under phase-transfer conditions with methyl iodide.

26: Same procedure as for 25 above starting with t-butylquinone.

20 and 19: The corresponding acid was converted to amide, which in turn was dehydrated to yield the nitrile.

18: This compound was made in four steps from gentisic acid by forming methyl ester 23, silylating the 4-hydroxyl group with a diphenyl-t-butyl silyl substituent, methylating the free hydroxyl group and removing the silyl substituent and the methyl ester group to give 18.

39: Prepared by methylation of corresponding phenolate anion.

42: Prepared in two steps from 3-methyl-4-nitrophenol by methylating the hydroxyl group followed by reduction of the nitro group to an amine group followed by methylation of the amine to yield the final product 42.

60: Prepared from 1,4-dihydroxynaphthalene in a manner similar to the preparation of 25.

Some general comments follow with regard to couplers that can be utilized in the present invention. Phenols and resorcinols do not trap oxidized dicarboxidine with the same efficiency as para-oxygen-substituted phenols and anilines. Unsubstitutes and alkyl-substituted hydroquinones do not trap oxidized dicarboxidine; they actually reduce it. Hydroquinones substituted with two or more electron-withdrawing groups have no effect on oxidized dicarboxidine. Para-methoxy anisole or ortho-methoxy anisole has no effect on oxidized dicarboxidine. Gentisic acid and 2-methoxy-5-hydroxy benzoic acid react with oxidized dicarboxidine, while 2-hydroxy-5-methoxy benzoic acid has no effect on oxidized dicarboxidine.

Analyte—the compound or composition to be measured, the material of interest. The analyte can be a peroxidatively active substance or it can directly or indirectly cause or inhibit peroxidatively catalytic activity. The analyte can be a member of a specific binding pair (sbp) and may be a ligand, which is mono- or polyvalent, usually antigenic or haptenic, and is a single compound or plurality of compounds which share at least one common epitopic or determinant site. The analyte can also be a component of a particle or can become bound to a particle during an assay. Exemplary of an analyte that is a component of a particle is an antigen on the surface of a cell such as a blood group antigen (A, B, AB, O, D, etc.) or an HLA antigen. Exemplary of an analyte becoming bound to a particle during an assay is an sbp member where a complementary sbp member is bound to a particle, glycoprotein or glycolipids where a lectin is bound to a particle, antibodies where protein A is bound to a particle, and the like. The binding involved when an analyte becomes bound to a particle can be specific or non-specific, immunological or non-immunological.

The polyvalent ligand analytes will normally be poly(amino acids), i.e., polypeptides and proteins, polysaccharides, nucleic acids, and combinations thereof. Such combinations include components of bacteria, viruses, chromosomes, genes, mitochondria, nuclei, cell membranes and the like.

The precise nature of some of the analytes together with numerous examples thereof are disclosed in U.S. Pat. No. 4,299,916 to Litman, et al., particularly at columns 16 to 23, the disclosure of which is incorporated herein by reference.

For the most part, the polyepitopic ligand analytes employed in the subject invention will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

A wide variety of proteins may be considered as to the family of proteins having similar structural features, proteins having particular biological functions, proteins related to specific microorganisms, particularly disease causing microorganisms, etc.

The monoepitopic ligand analytes will generally be from about 100 to 2,000 molecular weight, more usually from 125 to 1,000 molecular weight. The analytes of interest include drugs, metabolites, pesticides, pollutants, and the like. Included among drugs of interest are the alkaloids. Among the alkaloids are morphine alkaloids, which includes morphine, codeine, heroin, dextromethorphan, their derivatives and metabolites; cocaine alkaloids, which include cocaine and benzoyl ecgonine, their derivatives and metabolites, ergot alkaloids, which include the diethylamide of lysergic acid; steroid alkaloids; iminazoyl alkaloids; quinazoline alkaloids, isoquinoline alkaloids; quinoline alkaloids, which include quinine and quinidine; diterpene alkaloids, their derivatives and metabolites.

The next group of drugs includes steroids, which includes the estrogens, estogens, androgens, andreocortical steroids, bile acids, cardiotonic glycosides and aglycones, which includes digoxin and digoxigenin, saponins and sapogenins, their derivatives and metabolites. Also included are the steroid mimetic substances, such as diethylstilbestrol.

The next group of drugs is lactams having from 5 to 6 annular members, which include the barbituates, e.g. phenobarbital and secobarbital, diphenylhydantonin, primidone, ethosuximide, and their metabolites.

The next group of drugs is aminoalkylbenzenes, with alkyl of from 2 to 3 carbon atoms, which includes the amphetamines, catecholamines, which includes ephedrine, L-dopa, epinephrine, narceine, papaverine, and their metabolites.

The next group of drugs is benzheterocyclics which include oxazepam, chlorpromazine, tegretol, imipramine, their derivatives and metabolites, the heterocyclic rings being azepines, diazepines and phenothiazines.

The next group of drugs is purines, which includes theophylline, caffeine, their metabolites and derivatives.

The next group of drugs includes those derived from marijuana, which includes cannabinol and tetrahydrocannabinol.

The next group of drugs includes the vitamins such as A, B, e.g. $B_{12}$, C, D, E and K, folic acid, thiamine.

The next group of drugs is prostaglandins, which differ by the degree and sites of hydroxylation and unsaturation.

The next group of drugs is antibiotics, which include penicillin, chloromycetin, actinomycetin, tetracycline, terramycin, the metabolites and derivatives.

The next group of drugs is the nucleosides and nucleotides, which include ATP, NAD, FMN, adenosine, guanosine, thymidine, and cytidine with their appropriate sugar and phosphate substituents.

The next group of drugs is miscellaneous individual drugs which include methadone, meprobamate, serotonin, meperidine, amitriptyline, nortriptyline, lidocaine, procaineamide, acetylprocaineamide, propranolol, griseofulvin, valproic acid, butyrophenones, antihistamines, anticholinergic drugs, such as atropine, their metabolites and derivatives.

Metabolites related to diseased states include spermine, galactose, phenylpyruvic acid, and porphyrin Type 1.

The next group of drugs is aminoglycosides, such as gentamicin, kanamicin, tobramycin, and. amikacin.

Among pesticides of interest are polyhalogenated biphenyls, phosphate esters, thiophosphates, carbamates, polyhalogenated sulfenamides, their metabolites and derivatives.

Also included are hormones such as progesterone, testosterone, and so forth.

For receptor analytes, the molecular weights will generally range from 10,000 to $2\times10^8$ more usually from 10,000 to $10^6$. For immunoglobulins, IgA, IgG, IgE and IgM, the molecular weights will generally vary from about 160,000 to about $10^6$. Enzymes will normally range from about 10,000 to 1,000,000 in molecular weight. Natural receptors vary widely, generally being at least about 25,000 molecular weight and may be $10^6$ or higher molecular weight, including such materials as avidin, DNA, RNA, thyroxine binding globulin, thyroxine binding prealbumin, transcortin, etc.

Ligand analog or analyte analog—a modified ligand or ligand surrogate or modified analyte or analyte surrogate which can compete with the analogous ligand or analyte for a receptor, the modification providing means to join a ligand analog or analyte analog to another molecule. The ligand analog or analyte analog will usually differ from the ligand or analyte by more than replacement of a hydrogen with a bond which links the ligand analog or analyte analog to a hub or label, but need not. The term ligand surrogate or analyte surrogate refers to a compound having the capability of specifically binding a receptor complementary to the ligand or analyte. Thus, the ligand surrogate or analyte surrogate can bind to the receptor in a manner similar to the ligand or analyte. The surrogate could be, for example, an antibody directed against the idiotype of an antibody to the ligand or analyte.

Poly(ligand analog)—a plurality of ligand analogs joined together covalently, normally to a hub nucleus. The hub nucleus is a polyfunctional material, normally polymeric, usually having a plurality of functional groups, e.g., hydroxyl, amino, mercapto, ethylenic, etc. as sites for linking. The hub nucleus may be water soluble or insoluble, preferably water soluble, and will normally be at least about 30,000 molecular weight and may be 10 million or more molecular weight. Illustrative hub nuclei include polysaccharides, polypeptides (including proteins), nucleic acids, anion exchange resins, and the like. Water insoluble hub nuclei can also include walls of containers, e.g. glass or plastic, glass beads, addition and condensation polymers, Sephadex and Agarose beads and the like.

Member of a specific binding pair ("sbp member")—one of two different molecules, having an area on the surface or in a cavity which specifically binds to and is thereby defined as complementary with a particular spatial and polar organization of the other molecule. The members of the specific binding pair are referred to as ligand and receptor (antiligand). These will usually be members of an immunological pair such as antigen-antibody, although other specific binding pairs such as biotin-avidin, hormones-hormone receptors, nucleic acid duplexes, IgG-protein A, DNA-DNA, DNA-RNA, and the like are not immunological pairs but are included in the invention.

Ligand—any organic compound for which a receptor naturally exists or can be prepared.

Receptor ("antiligand")—any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, protein A, complement component Clq, and the like.

Label—A member of the signal producing system that is usually conjugated to an sbp member. The label can be isotopic or non-isotopic, usually non-isotopic, including catalysts such as an enzyme, a chromogen such as a fluorescer, dye or chemiluminescer, a radioactive substance, a particle, and so forth. In the methods of the present invention, at least one label is a peroxidatively active catalyst.

Signal Producing System—The signal producing system is utilized in assays for analytes and may have one or more components, at least one component being a label. The signal producing system generates a signal that relates to the presence or amount of analyte in a sample. The signal producing system includes all of the reagents required to produce a measurable signal. When the label is not conjugated to an sbp member analogous to the analyte, the label is normally bound to an sbp member complementary to an sbp member that is analogous to the analyte. Other components of the signal producing system can include substrates, enhancers, activators, chemiluminiscent compounds, cofactors, inhibitors, scavengers, metal ions, specific binding substances required for binding of signal generating substances, and the like. Other components of the signal producing system may be coenzymes, substances that react with enzymic products, other enzymes and catalysts, and the like. The signal producing system provides a signal detectable by external means, preferably by use of electromagnetic radiation, desirably by visual examination.

For purposes of the present invention, the signal-producing system includes at least one active catalyst, usually a peroxidase, and at least one substrate and may include two or more catalysts and a plurality of substrates, and may include a combination of enzymes, where the substrate of one enzyme is the product of the other enzyme. The operation of the signal producing system is to produce a product which provides a detectable signal related to the amount of analyte in the sample.

A large number of enzymes and coenzymes useful in a signal producing system are indicated in U.S. Pat. No. 4,275,149, columns 19 to 23, and U.S. Pat. No. 4,31.8,980, columns 10 to 14, which disclosures are incorporated herein by reference. A number of enzyme combinations are set forth in U.S. Pat. No. 4,275,149, columns 23 to 28, which combinations can find use in the subject invention. This disclosure is incorporated herein by reference.

Of particular interest are enzymes which involve the production of hydrogen peroxide and the use of the hydrogen peroxide to oxidize a dye precursor to a dye. Particular combinations include saccharide oxidases, e.g., glucose and galactose oxidase, or heterocyclic oxidases, such as uricase and xanthine oxidase, coupled with an enzyme which employs the hydrogen peroxide to oxidize a dye precursor, that is, a peroxidase such as horse radish peroxidase, lactoperoxidase, or microperoxidase. Additional enzyme combinations may be found in the subject matter incorporated by reference.

Non-specific binding—non-covalent binding between substances that is relatively independent of specific surface structures. Such non-specific binding will usually result from charge or electronic interactions between oppositely charged substances. Non-specific binding may also result from hydrophobic interactions between substances.

"Support"—a porous or non-porous water insoluble material. The support can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly(4-methylbutene), polystyrene, polymethacrylate, poly(ethylene terephthalate), nylon, poly(vinyl butyrate), etc.; either used by themselves or in conjunction with other materials; glass, ceramics, metals, and the like.

Sensitivity—is used in the sense of detection limit, i.e., the smallest amount of a peroxidatively active catalyst, e.g., HRP, giving a signal that is distinguishable from the signal obtained in the absence of the peroxidatively active catalyst.

Ancillary Materials—various ancillary materials will frequently be employed in an assay in accordance with the present invention. For example, buffers will normally be present in the assay medium, as well as stabilizers for the assay medium and the assay components. Frequently, in addition to these additives, additional proteins may be included, such as albumins, or surfactants, particularly non-ionic surfactants, binding enhancers, e.g., polyalkylene glycols, or the like.

The present invention has particular application to the determination of an analyte in a sample suspected of containing such analyte. The present assay method has application both to heterogeneous and homogeneous assays. Exemplary of heterogeneous assays are the radioimmunoassay (RIA, Yalow and Berson, *J. Clin, Invest.* (1960) 39, 1157), and enzyme immunoassays (EIA) such as the enzyme linked immunosorbant assay (ELISA), see "Enzyme-Immunoassay" by Edward T. Maggio, CRC Press Incorporated, Boca Raton, Fla., 1980. Homogeneous immunoassays are exemplified by enzyme multiplied immunoassay techniques (e.g. see U.S. Pat. No. 3,817,837), immunofluorescence methods such as those disclosed in U.S. Pat. No. 3,993,345, enzyme channeling techniques such as those disclosed in U.S. Pat. No. 4,233,402, and other enzyme immunoassays as discussed in Maggio, Supra. The disclosures of the above references are incorporated herein in their entirety.

The assay for a peroxidatively active catalyst or for an analyte will normally be carried out in an aqueous buffered medium at a moderate pH, generally that which provides optimum sensitivity. The assay can be performed either without separation (homogeneous) or with separation (heterogeneous) of any of the assay components or products.

The aqueous medium may be solely water or may include from 0 to 40 volume percent of a cosolvent. The pH for determination of a peroxidatively active catalyst is usually about 4 to 6, preferably 4.5–5.5. For maximum color generation and to obtain a precipitable product, a pH of about 4.5 is preferred. For a soluble product, which finds utility in homogeneous assays, a pH of about 5.5 is preferred. However, at higher pH's, the sensitivity of the determination is reduced. Thus, a balance of these factors should determine the particular pH employed. In some circumstances, the reaction can be conducted at a pH of 4 to 6 and detection, such as of fluorescence, can be conducted at pH 7–10, preferably 8 to 9.

The pH for the medium for assays for analytes that are sbp members will usually be in the range of about 4 to 11, more usually in the range of about 5 to 10, and preferably in the range of about 6.5 to 9.5. The pH will usually be a compromise between optimum binding of binding members and the pH optimum for other reagents of the assay such as members of the signal producing system.

Various buffers may be used to achieve the desired pH and maintain the pH during the determination. For the determination of a peroxidatively active catalyst an alkyl carboxylate buffer such as adipate, citrate, acetate, or the like, is preferred. Numerous other buffers can be employed. Illustrative buffers include borate, phosphate, carbonate, tris, barbital and the like. The particular buffer employed in an assay for an analyte is not critical, but in an individual assay one or another buffer may be preferred. Another factor is the storage stability of the various benzidines and couplers where particular buffers such as adipate may be selected over others to achieve maximum storage stability.

Moderate temperatures are normally employed for carrying out the reactions for determination of a peroxidatively active catalyst and/or for an sbp member and usually constant temperatures during the period of a measurement are employed. Incubation temperatures will normally range from about 5° to 45° C., more usually from about 15° to 40° C. Temperatures during measurements will generally range from about 10° to 50°, more usually from about 15° to 40° C.

As mentioned above, the present invention provides for enhanced sensitivity for the determination of a peroxidatively active catalyst. The concentration of such catalyst that may be determined will generally vary from $10^{-19}$M to $10^{-8}$M, more usually from $10^{-16}$M to $10^{-11}$M. The concentration of a benzidine will usually be from $10^{-6}$M to $10^{-2}$M, preferably $10^{-5}$M to $10^{3}$M. The concentration of a coupler will usually be from $10^{-5}$M to $10^{-1}$M, preferably $10^{-4}$M to $10^{-2}$M. The concentration of a hydroperoxide will usually be from $10^{-5}$M to 1M, preferably $10^{-4}$M to $10^{-1}$M.

The concentration of analyte which may be assayed will generally vary from about $10^{-4}$ to $10^{-15}$M, more usually from about $10^{-6}$ to $10^{-14}$M. Considerations, such as whether the assay is qualitative, semiquantitative or quantitative, the particular detection technique and the concentration of the analyte of interest will normally determine the concentrations of the various reagents.

While the concentrations of the various reagents in the medium will generally be determined by the concentration range of interest, the final concentration of each of the reagents will normally be determined empirically to optimize sensitivity. That is, a variation in concentration of the catalyst or of the analyte which is of significance should provide an accurately measurable signal difference.

For immunoassays, while the order of addition of reagents may be varied widely, there will be certain preferences depending on the nature of the immunoassay. The simplest order of addition is to add all the reagents simultaneously. Alternatively, the reagents can be combined sequentually.

Optionally, an incubation step may be involved subsequent to each addition, generally ranging from about 30 seconds to 6 hours, more usually from about 2 minutes to 1 hour. Generally, in an assay for an analyte the assay is carried out to the point of determining a signal in relation to the presence of analyte, at which point the reagents for conducting the determination in accordance with the present invention are added. All these reagents must be present at the same time to produce a signal, which is then determined.

The products of the reaction can be monitored by direct observation of the reaction medium, either visually or instrumentally, or a reagent can be added to enhance the detectibility of the product as, for example, a higher pH buffer or a hydrophobic surface to enhance the fluorescent signal.

The present invention is exemplified, by way of illustration and not limitation, by a system utilizing dicarboxidine 11 as the benzidine and gentisic acid 17 as the coupler.

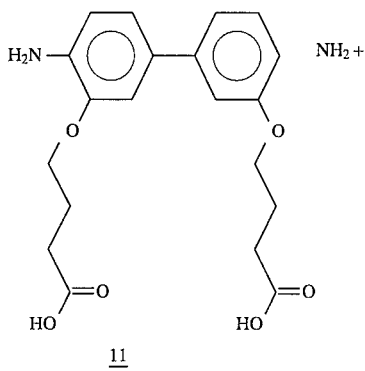

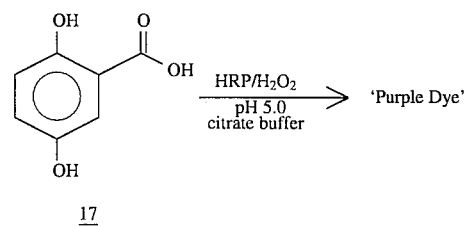

The oxidative coupling reaction of dicarboxidine and gentisic acid forms a precipitable purple dye. A number of gentisic acid derivatives 34, 35, 36, and 37 were prepared by the reaction of the NHS-ester of gentisic acid with the corresponding amine. In solution, all of these gentisic acid derivatives trapped oxidized dicarboxidine with approximately the same relative rate as gentisic acid 17.

The merocyanine dyes formed from 35, 36, and 37 came out of solution much faster than the merocyanine dye formed from gentisic acid 17. Thus, charge neutralization to enhance precipitability of the resulting dye leads to more precipitable products.

To the extent that any particular theories are referred to herein, the present invention has been demonstrated and should, therefore, not be restricted to any particular theory.

Various specific embodiments employing the methods of the present invention will next be described using dicarboxidine by way of example and not limitation. Dicarboxidine (11) on oxidation with HRP/$H_2O_2$ couples with, e.g., gentisic acid 17 to form merocyanine dyes.

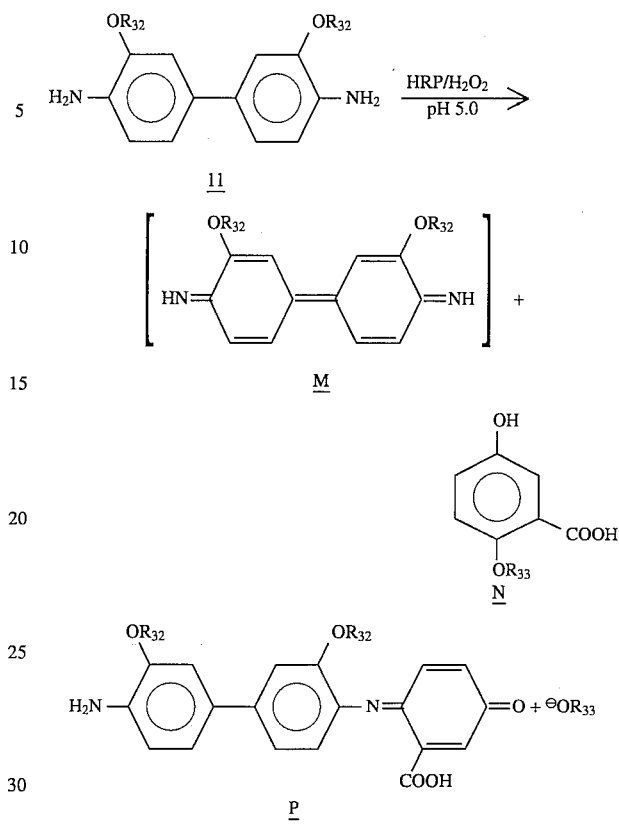

wherein:

$R_{32}=(CH_2)_3-CO_2H$ and $R_{33}=R_{32}$, alkyl, $CH_2-CO_2H$ or a fluorophore, luminescer or absorptive species.

The reaction proceeds in almost quantitative yield. $\theta OR_{33}$ can be an absorptive, luminescent or a fluorescent species. By the above reaction, a mole of fluorescent moiety is generated per mole of dye formed. The detection of fluorophores is much more sensitive. Therefore, by attaching a fluorophore to the phenol or aniline, an extremely sensitive HRP-labeled detection system is obtained.

Umbelliferone derivates are exemplary of such substrates. Umbelliferone derivatives have been routinely used as fluorescent detection agents for reporter enzymes like β-galactosidase and alkaline phosphatase. Umbelliferone derivatives can be prepared, for example, in a manner similar to that used to prepare umbelliferone derivatives in European Patent Specification 0 060 518. 51 was prepared by reacting the anion of umbelliferone with 4-fluoronitrobenzene followed by reduction with Zn/HCl. 48 was prepared by hydrolysis of diazotized 51.

The HRP assay is preferably conducted at the substrate's most stable formulation and where HRP is most active, i.e., pH 3.5 to 7, preferably about 5.0, and the fluorescence detection is recorded at pH which is dependent on the particular fluorophore and can be in the range of about 4 to 11, preferably about 7 to 9, more preferably about 8. HRP can thus be detected at a level of 1 pg/ml or less of HRP in two minutes.

The present invention may be used in a system involving generation of two dyes as exemplified (by way of illustration and not limitation) in the following reaction scheme:

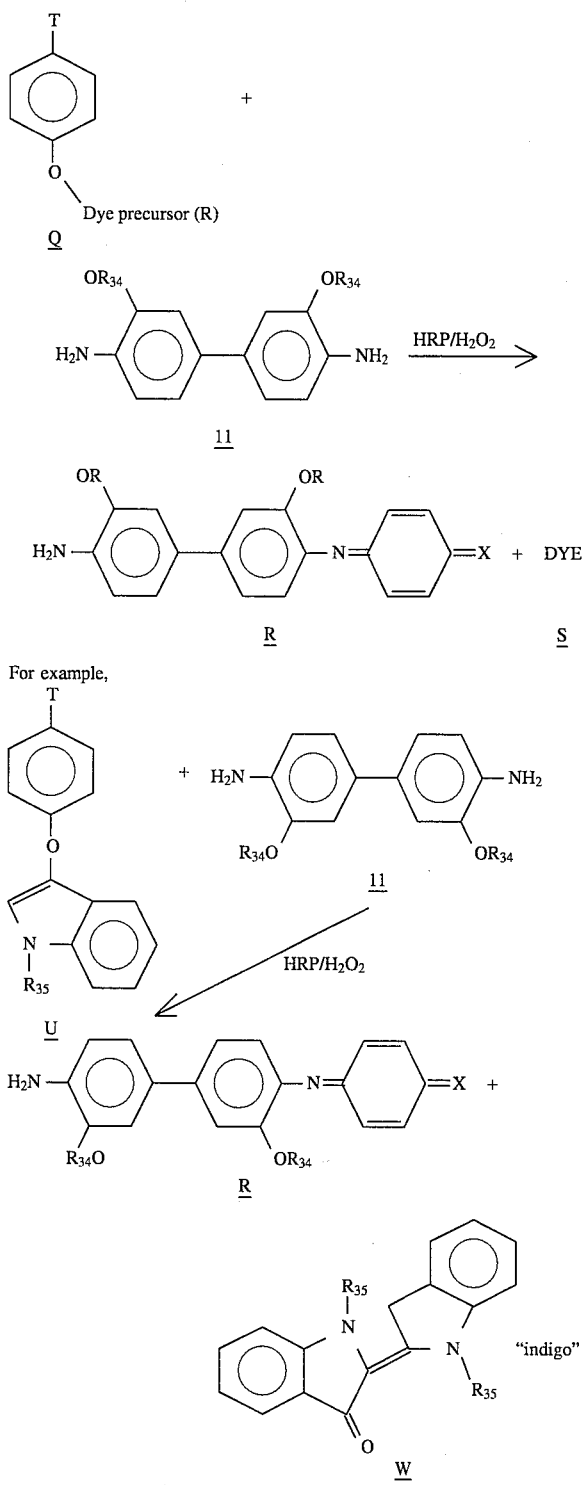

wherein $R_{34}$ is $(CH_2)_3CO_2H$ and T is OH and $R_{35}$ is H or alkyl.

Oxidized dicarboxidine couples regioselectively at the position on the ring of Q para to T. Q is a dye precursor and the oxidating coupling of Q with 11 gives R and dye S. The color generated can be additive and the sensitivity of the system at a given wave length enhanced if the absorption maxima of S and R overlap.

One particular embodiment of the present invention involves the detection of molecules such as, e.g., antigens, by means of a sandwich immunoassay. In the method for detection of antigens an immune sandwich complex is formed comprising the antigen, a first antibody (monoclonal or polyclonal) that binds to the antigen and a second antibody that binds to the antigen. Subsequently, the immune sandwich complex is detected and is related to the amount of the antigen analyte in the sample. The immune sandwich complex is detected by virtue of the presence in the complex of a peroxidatively active catalyst label wherein either or both the first antibody and the second antibody contain labels or substituents capable of combining with labels, such as, for example, linking the antibody to biotin and providing avidin bound to a label.

The immune sandwich complex assays for antigens are well known and protocols for such assays may utilize the present invention. Such sandwich type assays are disclosed in, for example, U.S. Pat. No. 4,486,530, the disclosure of which is incorporated herein by reference in its entirety. The immune sandwich complex assay may be conducted by having the second antibody bound to a support. The immune sandwich complex thus becomes bound to a support if the antigen analyte is present in the sample. The sample suspected of containing the analyte can be combined with the first antibody and the combination subsequently combined with the second antibody. On the other hand, the reagents can be combined simultaneously. After separation of the support from the medium, the support is combined with a peroxide, a benzidine, and a coupler in accordance with the present invention. A signal is then determined.

Another example of an assay in which the present invention may be employed is described in U.S. Pat. No. 4,879,214. The disclosure of this patent is incorporated herein by reference in its entirety. The method and device are for determining the presence of an analyte in a sample suspected of containing the analyte. The method involves providing in combination a test solution containing the sample, a first member of a specific binding pair and a contact portion of a test strip of bibulous material capable of being traversed by the test solution by means of capillary action. The first member of the specific binding pair can be capable of binding the analyte. The strip contains a second member of a specific binding pair integral therewith for concentrating and non-diffusively binding the first specific binding pair member at a small situs on the strip separated from the contact portion of the strip. The strip can further contain a third sbp member between the small situs and the contact portion. A detectible signal is produced in relation to the presence of the analyte in the test solution. Applying the present invention to the method and device above, the small situs can contain, after the running of the assay, a peroxidatively active catalyst. A peroxide, a benzidine, and a coupler are contacted with the situs to generate a signal at the situs as a result of the presence of the peroxidatively active catalyst, whose presence is related to the presence of the analyte.

Another aspect of the present invention is a compound of the formula

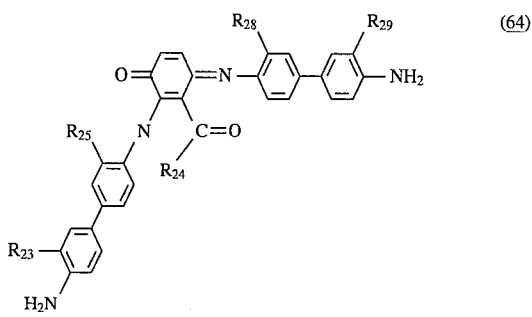

wherein:

$R_{24}$ is OH, $NH_2$, $N(alkyl)_2$, or $NH(CH_2)_2NH(CH_2)_2NH_2$, and $R_{25}$ is alkyl, O-alkyl, or O-carboxyalkyl.

Another aspect of the invention is a compound of the formula

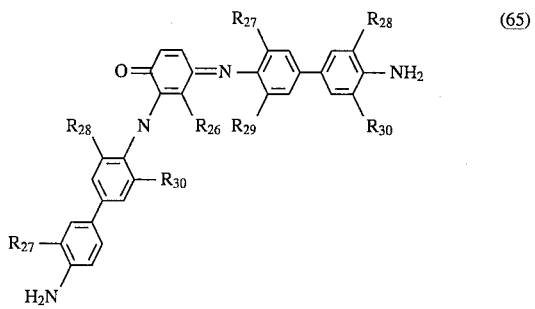

wherein:

$R_{26}$ is CN, Cl, $COOR_{31}$ wherein $R_{31}$ is H or lower alkyl, $R_{27}$ and $R_{28}$ are independently H, $-CH_3$, $-OCH_3$, or $-O(CH_2)_3CO_2H$, and $R_{29}$ and $R_{30}$ are independently H or $-CH_3$ with the proviso that one of $R_{27}$ or $R_{29}$ must be H.

The above compounds are synthesized from the appropriate benzidine and phenol according to the following exemplary scheme:

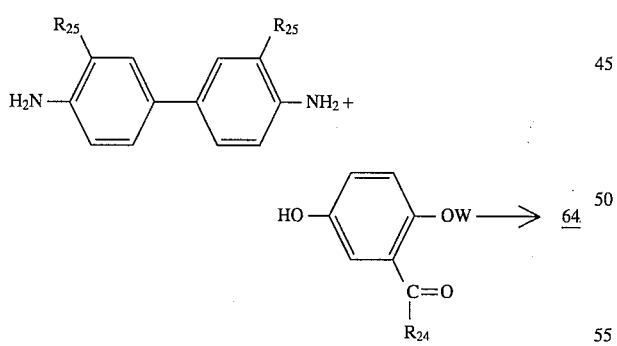

wherein OW is a leaving group.

To enhance the versatility of the subject invention, the reagents can be provided in packaged combination, in the same or separate containers, in liquid or lyophilized form so that the ratio of the reagents provides for substantial optimization of the method and assay. The kit comprises a source of a hydroperoxide, a benzidine, and a coupler as herein described. The kit can further include other separately packaged reagents for conducting an assay including members of other signal producing systems, binding agents such as antibodies, DNA probes, etc. The reagents can be separately contained or one or more can be combined in a single container depending on the cross-reactivity of such reagents.

EXAMPLES

The invention is further described by the following illustrative examples. Parts and percentages herein are by weight unless otherwise indicated. Temperatures are in degrees Centigrade (°C.).

In the examples, the following abbreviations are used:

DCC—dicyclohexylcarbodiimide
THF—tetrahydrofuran
hr—hour
eq—equivalent
mg—milligram
TLC—thin layer chromatography
$^1$H-NMR—$^1$H nuclear magnetic reconance
IR—infrared
m—muitiplet
d—doublet
d,d—doublet of doublets
t—triplet
s—singlet
Bu—butyl
EtoAc—ethyl acetate
Me—methyl
TFA—trifluoroacetic acid
DMF—dimethylformamide
MeOH—methyl alcohol
DMSO—dimethylsulfoxide
NHS—N-hydroxysuccinimide
EtOH—ethanol
PSI—pounds per square inch
L.C.—liquid chromatography
F.U.—fluorescence unit
DCU—dicyclohexylurea

EXAMPLE 1

Preparation of Various Amides of Gentisic Acid 335 mg (1 eq) of gentisic acid XIX, 278 mg (1.1 eq) of NHS and 568 mg of DCC were stirred in 15 mL of dry THF at room temperature for 16 hours. At this time TLC indicated that all the gentisic acid was consumed (TLC in ethyl acetate). DCU was filtered off, and the THF solution of the NHS ester of gentisic acid 17 was added to 1.2 equivalents of various amines (1.2 eq) (a–d below) in dry THF. The reaction solution was stirred for 12 hours, the solvent was evaporated, and the product was crystallized from the methanol-ethyl acetate (1:1) mixture.

(a) Amine=di(aminoethyl)amine gave 36 in 76% yield.
$^1$H-NMR (CDCl$_3$): σ 2.1 (m, 6H), 2.6 (m, 2H), 6.8 (6, 1H), 7.0 (d,d,1H), 7.3 (d, 1H). IR—(Nujol): 3300 cm$^{-1}$, 1670 cm$^{-1}$ (S)

(b) Amine=diethylenediaminoethylamine gave 37 in 8% yield. $^1$H-NMR (CDCl$_3$): σ 2.2 (m, 10H), 2.65 (m, 2H), 6.8 (d, 1H), 7.0 (d,d,1H), 7.3 (d, 1H). IR—(Nujol): 3300 cm$^{-1}$, 1670 cm$^{-1}$ (S)

(c) Amine=dimethylaminoethylamine gave 35 in 88% yield. $^1$H-NMR (CDCl$_3$): σ 2.5 (m, 10H), 2.7 (m, 2H), 2.656 (s, 6H), 6.8 (d,d,1H), 7.0 (d,d, 1H), 7.3 (d, 1H). IR—(Nujol): 1670 cm$^{-1}$ (S)

(d) Amine=ammonia gave 34 in 97% yield.

Ammonia was bubbled through THF solution for 1 hr at −20° C. $^1$H-NMR (CDCl$_3$): σ 6.8 (d, 1H), 7.0 (d,d, 1H), 7.3 (d, 1H). IR—(Nujol): 1630 cm$^{-1}$

EXAMPLE 2

Preparation of Methyl Ester 22 of Gentisic Acid and 3-Methyl Ether 23 Derivative Thereof (a) Gentisic acid 17 (1.54 g) was taken up in 25 mL of dry methanol, 0.2 mL of trimethyl silyl chloride was added, and the solution was refluxed for 12 hr. The solvent was then evaporated to yield the methy ester 22 in almost quantitative yield. $^1$H-NMR (acetone d$_6$): σ 3.95 (s,3H), 6.75 (d,1H), 7.0 (d,d 1H), 7.25 (d, 1H)

(b) 23 was prepared by a similar procedure to (a) above.

Yield: quantitative $^1$H-NMR- (CDCl$_3$): σ 3.7 (s, 3H), 3.95 (s, 3H), 6.8 (d, 1H), 7.05 (d,d,1H), 7.25 (d, 1H).

EXAMPLE 3

Preparation of 6-Methoxy-3-Hydroxybenzoic Acid 18

(a) To a stirred solution of NaH (washed three times with dry THF to remove oil, 0.29 g [2.2 eq]) in dry DMF (10 mL, CaH$_2$ dried), gentisic acid methyl ester 22 (0.42 g [1.0 eq ] in 3 mL of dry DMF) is added over a period of 5 minutes at −40° C. under argon. The reaction mixture was allowed to warm to room temperature in 1 hr. t-Butyl diphenylchlorosilane (0.7 g [1.1 eq ] in 2 mL of dry DMF) was added over a period of 10 minutes. The reaction mixture was allowed to stir at room temperature for 16 hr., at which time TLC indicated the absence of starting material. Dichloromethane (200 mL) was added, and the organic layer was extracted with water (2×100 mL) and brine (3×100 mL), respectively. The organic phase was dried over Na$_2$SO$_4$. The solvent was removed under reduced pressure to yield a crude product, which was purified by column chromatography (SiO$_2$, 230–400 mesh, hexane ethyl acetate 1:1) to yield pure diphenyl-t-butylsilyl product (A) (800 mg, 79%).

$^1$H-NMR (acetone d$_6$): σ 1.0 (s, 9H), 3.8 (s, 3H), 6.65 (d, 1H), 6.9 (d,d, 1H) 7.2 (d, 1H) 7.6 (m, 10H).

(b) 406 mg of A (1 eq), 0.125 mL of methyl iodide (2 eq), and 150 mg of potassium carbonate were stirred in 20 mL of DMF for 24 hr., under argon, at which time TLC indicated the absence of 1. To this stirred solution, 150 mg of potassium carbonate and 5 mL of water were added and the reaction mixture stirred under argon for 2 hr. Dilute HCl was added to neutralize the reaction mixture, and then 250 mL of water were added and the reaction mixture was stirred under argon for 2 hr. Dilute HCl was added to neutralize the reaction mixture, and then it was added to 250 mL of methylene chloride and extracted with brine (3×150 mL), dried over Na$_2$SO$_4$, solvent evaporated under reduced pressure to yield crude product which was purified on silica gel (230–400 mesh, ethylacetate: methylene chloride, 1:1) to yield pure 3-diphenyl-t-butylsiloxy-6-methoxybenzoic acid product (B), 332 mg, 82%.

$^1$H-NMR: (acetate d$_6$): σ 1.0 (s,9H), 3.85 (s, 3H), 6.85 (d, 1H), 7.0 (d,d, 1H), 7.3 (d, 1H), 7.6 (m, 10H).

(c) 325 mg of B (1 eq), 420 mg of tetrabutylammonium fluoride (2 eq) were stirred in dry THF under argon for 4 hr. Ethyl acetate (100 mL) was added, and the organic layer was extracted with brine (5×100 mL). The organic phase was dried over Na$_2$SO$_4$ and solvent evaporated under reduced pressure to yield crude product, which was purified over silica gel (230–400 mesh, EtocAc) to yield 126 mg of 18 (92%).

$^1$H-NMR (CDCl$_3$/pyridine): σ 3.9 (s, 3H), 6.9 (d, 1H), 7.0 (d, 1H), 7.3 (d, 1H).

EXAMPLE 4

Preparation of 2,6-Dimethyl-4-Methoxyphenol 25

A mixture of 10 mL of CH$_2$Cl$_2$, 10 mL of H$_2$O, 460 mg of 2,6-dimethylhydroquinone, 200 mg of NaOH, 940 mg (2 eq) of methyl iodide, and 760 mg of benzyl triethyl ammonium bromide in CH$_2$Cl$_2$/H$_2$O (C) were stirred at room temperature under argon for 12 hr. Dilute HCl was added to adjust the pH to 7.0, followed by 200 mL of CH$_2$Cl$_2$, and the organic layer was extracted with brine (5×100 mL), dried over Na$_2$SO$_4$, the solvent evaporated under reduced pressure, and the crude product was applied to silica gel (230–400 mesh, CH$_2$Cl$_2$) to yield 356 mg of product 25, about 70% yield.

$^1$H-NMR (CDCl$_3$) σ 2.2 (s, 6H), 3.6 (s, 3H), 6.5 (s, 2H)

EXAMPLE 5

Preparation of 2,3,5,6-Tetramethyl-4-carboxymethoxyphenol 27

A mixture of 20 mL of CH$_2$Cl$_2$, 20 mL H$_2$O, 415 mg (1 eq) of tetramethylhydroquinone (D), 200 mg of NaOH, 540 mg (1.1 eq) of t-butylbromoacetate, 760 mg of C were stirred at room temperature, under argon, for 12 hr. Initially, D was not completely soluble, but with time, in 1 hr, it completely dissolved. After 12 hr, acid was added to bring the pH to 7.0, 200 mL of CH$_2$Cl$_2$ was added, and the reaction mixture was extracted with brine (4×200 mL), dried over Na$_2$SO$_4$, and evaporated under reduced pressure to yield crude product. 5 mL of TFA was added to the crude product, and the mixture was stirred for 1 hr. TFA was evaporated and the crude product charged on silica gel (230–400 mesh, CH$_2$Cl$_2$-EtOAc, 2:1) to yield 270 mg (49%) of product 27.

$^1$H-NMR (CDCl$_3$) σ 1.9 (s, 6H), 2.0 (s, 6H), 4.05 (s, 2H).

EXAMPLE 6

Preparation of 3-Methoxy-6-Aminobenzoic Acid 39

To a stirred solution of NaH (washed three times with dry THF to remove oil, 0.145 g, 1.1 eq) in dry DMF (5 mL, CaH$_2$ dried), 420 mg of methyl 3-hydroxy- 6-aminobenzoate (E) was added in 3 mL of DMF immediately followed by MeI (443 mg [0.195 m], 1.2 eq), and stirred at room temperature under argon for 16 hr, at which time TLC indicated the absence of E. 200 mL of CH$_2$Cl$_2$ was added and the mixture was extracted with brine (5×100 ml); the organic solvent was evaporated; the crude product was added to 200 mg of NaOH in 5 mL of water; and the reaction mixture was heated at 70° C. for 2 hr. The reaction mixture was neutralized to pH 7.0 with dilute HCl and extracted with $CH_2Cl_2$ (5×25 mL). The organic layer was dried over $Na_2SO_4$ and evaporated under reduced pressure to yield crude product, which was applied to silica gel (230–400 mesh and eluted with EtOAc/MeOH, 50:1) to yield product 39, 206 mg (yield 45%).

$^1$H-NMR (DMSO) σ 4.25 (s, 3H), 7.15 (d,1H), 7.4(d,d, 1H), 7.7 (d, 1H).

EXAMPLE 7

Preparation of 2-Methyl-4-Methoxy-N,N-dimethylaniline 42

0.835 g of 2-methyl-4-methoxynitrobenzene was dissolved in 50 mL of ethanol. To this solution 5 mL of 7% aq. formaldehyde solution was added along with 50 mg of 5% Pd/C catalyst and hydrogenated under 60 PSI of $H_2$. Within two hours, the pressure dropped from 60 PSI and the reaction mixture was agitated overnight. The catalyst was filtered off and the solvent evaporated under reduced pressure. The crude material was dissolved in aqueous HCl and washed with ether (3×100 mL) to remove neutral materials. The acidic aqueous solution was neutralized and extracted with ethyl acetate (4×50 mL). The organic layer was dried over $Na_2SO_4$ and evaporated under reduced pressure to yield 790 mg of product 42. Yield 795%.

$^1$H-NMR ($CDCl_3$): σ 2.25 (s, 3H), 2.6 (s, 6H), 3.75 (s, 3H), 7.0 (m, 3H).

EXAMPLE 8

Preparation of Carbomethoxyquinone (F)

420 mg (1 eq) of 23 and 180 mg of $PbO_2$ (3 eq) with 10 mL of dry toluene (CaH, dry) were placed in a 20 mL round bottom flask in an oil bath and heated at 60° C. with stirring under argon for 12 hr. The catalyst was filtered off and toluene was added to 70 mL of carbon disulfide and F crystallized out as orange crystals.

M.P.=52°–54° C. Yield 42%. $^1$H-NMR ($CDCl_3$): σ 3.95 (s,3H), 6.85 (d, 1H), 7.0 (d,d,1H), 7.3 (d,1H). IR (Nujol): 1720 $cm^{-1}$, 1660 $cm^{-1}$.

EXAMPLE 9

Preparation of 2-Cyanohydroquinone 20

Trifluoroacetic anhydride (3.06 mL, 22 mmoles) was added dropwise to a stirred, ice-cooled solution of 34 (770 mg, 5.0 mmoles) in 10 mL of dry THF and anhydrous pyridine (3.23 mL, 40 mmoles) at such a rate that the temperature was kept below 5° C. The addition was over in 30 minutes. The reaction mixture was then allowed to warm to room temperature and stirred for another 16 hr. 650 mL of $CH_2Cl_2$ was added and the organic solution was washed with water (3×10 mL) and saturated brine (3×15 mL), dried on $Na_2SO_4$ and evaporated under reduced pressure. The crude product was applied to silica gel (230–400 mesh, ethyl acetate) to yield 462 milligrams (68%) of 20.

$^1$H-NMR (acetone $d_6$): σ 7.25 (d, 1H), 7.6 (d, 1H), 7.75 (broad, s,1H). IR (Nujol): 2250 $cm^{-1}$, 1500 $cm^{-1}$.

EXAMPLE 10

Preparation of 3-Cyano-4-methoxyphenol 19

XL was prepared in a similar manner as 20 was prepared in Example 9 starting with 2-methoxy-5-hydroxybenzoamide. Yield 62%

$^1$H-NMR ($CDCl_3$): σ 3.8 (s, 3H) 7.0 (m, 2H), 7.4 (broad singlet 1H). IR (Nujol): 2250 $cm^{-1}$, 1500 $cm^{-1}$.

EXAMPLE 11

Reaction of 2,2'-Dimethylbenzidine 9 and Various Couplers a. Reaction with 17:

53 mg of 9 (1 eq) and 52 mg of 17 (1.25 eq) were taken in 250 mL of citrate buffer (0.1M, pH 5.0, concentration of reactants 1 mM and 1.25 mM) and stirred at room temperature; 0.01 mg of HRP and 2.5 mL of 1M $H_2O_2$ were added. The buffer immediately turned purple. The reaction was allowed to proceed for 1 hr. The buffer solution was then extracted with ethyl acetate (10×50 mL). The ethyl acetate layer was washed once with brine (1×100 mL), dried over $Na_2SO_4$ and evaporated under vacuum to yield a purple paste. The crude product was immediately applied to a preparative TLC plate and developed with ethyl acetate. Two purple bands were isolated (extracted with ethyl acetate). Approximately 2.5 mg of major G and 0.2 mg of minor product H were isolated under the present conditons. The compound is stored at 0° C. in the absence of light and under argon.

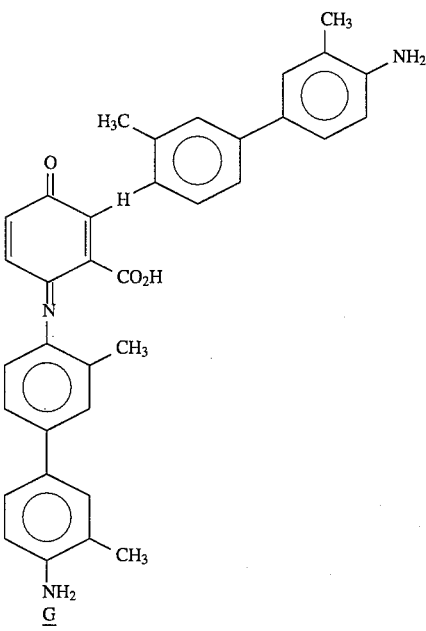

+

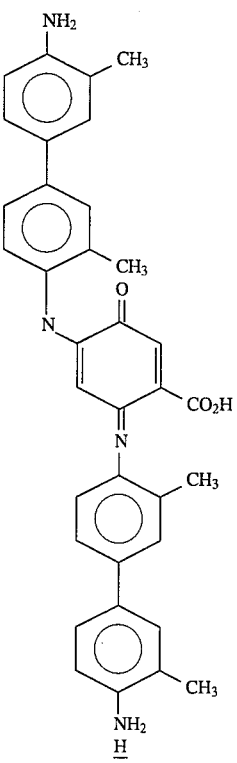

(b) Reaction with 18:

The reaction and the workup were carried out as described above for (a). Products G and H were obtained.

(c) Reaction with 26:

The reaction and the workup were carried out as described above for (a). Product J was obtained.

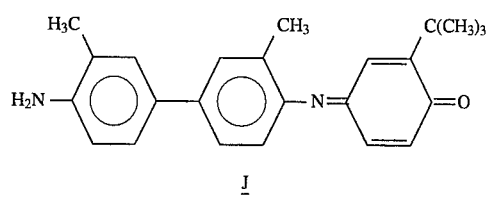

(d) Reaction with 41:

The reaction and the workup were carried out as described above for (a). Product K was obtained.

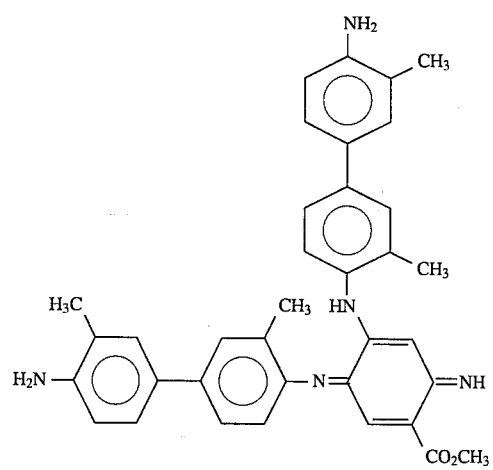

(e) Reaction with 38:

The reaction was carried out in a similar manner as described above. The reaction flask was transferred to a refrigerator to precipitate the product. The buffer was drained and the pasty-brown solid was washed with water (1×100 mL) and dissolved in a mixture of methanol and ethyl acetate (1:5) (10×100 mL). Even under these conditions very little product was extracted into the organic layer. The solvent was evaporated and the product purified on preparative L.C. to obtain 1 to 2 milligrams of product K (the carboxylic acid group of the product of this reaction was esterified during the workup; thus K was obtained).

(f) Reaction with 39:

The reaction and the workup were carried out or described above for (e). Product L was obtained.

Spectral Features

Compound G:

Mass Spectrum: FAB-M+2H+1-559 DCI (NH$_3$)-M+1-44 - 513 $^1$H-NMR (CD$_2$Cl$_2$) δ: 2.25 (s,3H), 2.26 (s,3H), 2.3 (s, 3H), 2.32 (s, 3H), 6.1 (d,1H), 6.32 (d,1H), 6.34 (d,1H), 6.45 (d, 1H), 6.55 (d,1H), 6.82 (d,1H), 6.9–7.1 (8H) I.R. - Nujol - cm$^{-1}$: 3320 (w), 1680 (m), 1600 (m, broad). U.V. - citrate buffer pH 5.0, 0.1M - 586 nm (18200).

Compound H:

$^1$H-NMR (CD$_2$Cl$_2$) δ: 2.15 (s,3H), 2.16 (s,3H), 2.25 (s,3H), 2.28 (s,3H) 5.62 (s,1H), 6.66 (d,1H), 6.69 (d,1H) 7.0 (d,1H), 7.2–7.4 (10H). I.R. (neat) cm$^{-1}$: 3350 (w), 1680 (m), 1600 (m, broad). U.V. - citrate buffer pH 5.0, 0.1M - 520-520 nm (.16,000).

Spectral Features - continued

Compound J:

Mass Spectrum - DCI (NH$_3$) - M+1- 359. $^1$H-NMR (CD$_2$Cl$_2$) δ: - 1.1 (s), 1.25 (s) [9H], 2.15 (s,6H), 6.3 (d), 6.45 (d), 6.51 (d), 6.55 (d), 6.65 (d,d) 6.85 (d), 7.1–7.4 [9H]. I.R. (Neat cm$^1$ - 3400 (w), 1640 (m), 1600 (m, broad). U.V. (citrate buffer pH 5.0, 0.1M) - 512 nm (10700.

Compound K:

Mass Spectrum - DCI (NH$_3$) - M+NH$_4$ or M+18 - 587. $^1$H-NMR (CD$_2$Cl$_2$) δ: 2.15 (s,3H), 2.17 (s,3H), 2.25 (s,3H), 2.27 (s,3H), 2.9 (s,3H), 5.79 (s,1H), 6.65 (d,1H), 6.69 (d,1H), 6.92 (d,1H), 7.2–7.4 (10H). I.R. (Neat) cm$^{-1}$- 3370 (w), 1695 (m), 1600-1500 (m, broad). U.V. (citrate buffer pH 5.0, 0.1M) - 420 nm (21000).

EXAMPLE 12

Sensitivity of Substrate System

This experiment was designed to determine the lowest amount of HRP that was detectable in a particular time frame (30 minutes).

Procedure

| Stock Solutions: | |
| --- | --- |
| Dicarboxidine | 12 mg/mL - 26 mM |
| Gentisic Acid | 6 mg/mL - 39 mM |

Potassium Citrate 0.1M —pH adjusted with dilute HCl to 4.5 (±0.1)

HRP—absorption at 403 nm was determined; the sample was then diluted appropriately to obtain a stock solution of 10 ng/mL.

$H_2O_2$—100 mM stock solution Experiments were run in triplicate; in a typical experiment, 0.05 mL of dicarboxidine 11, 0.03 mL of gentisic acid 17, 0.05 mL of hydrogen peroxide and HRP (0.000 mL to 0.02 mL) were added to buffer (0.87 to 0.85 mL) in that order to start the reaction. The results are summarized in Table 1.

TABLE 1

|   | [HRP] pg | [$H_2O_2$] Mm | Absorbance at 550 nm (OD × 1000) |
|---|---|---|---|
| 1. | 0 | 0 | 20 ± 8 |
| 2. | 0 | 5 | 31 ± 3 |
| 3. | 10 | 5 | 32 ± 6 |
| 4. | 20 | 5 | 39 ± 4 |
| 5. | 30 | 5 | 53 ± 3 |
| 6. | 40 | 5 | 71 ± 5 |
| 7. | 50 | 5 | 84 ± 6 |
| 8. | 100 | 5 | 138 ± 7* |
| 9. | 200 | 5 | 255 ± 20* |

*slight precipitation

At 100 pg/mL of HRP, there was slight precipitation of the product dye. Therefore, these absorbance numbers were underestimated. The data indicate that 30 pg/mL of HRP can be detected in 30 minutes under the appropriate conditions.

30 pg/mL - 22±3 absorbance units

EXAMPLE 13

Release of Fluorophore

| Stock Solutions | |
|---|---|
| 49 | 1 mM solution in DMSO |
| Dicarboxidine 11 | 10 mM solution in $H_2O$ |
| 2-chloro-4-diethyl-aminoaniline (XV)* | 10 mM solution in $H_2O_2$ |
| $H_2O_2$ | 125 mM solution in citrate buffer pH 5.0 (0.1M). Solution made just before use. |
| HRP | The concentration adjusted, based on absorption at 403 nm ($\epsilon$ 102 $mM^{-1}$ $cm^-$, −10 ng/ml and 100 ng/mL (pH 7). |

*For purposes of comparison, not in accordance with the present invention.

(a) pH Jump Method 0.01 mL of dicarboxidine 11 (or XV), 0.1 mL of 49 and 0.04 mL of $H_2O_2$ were added to 0.75 mL (0.76 mL) citrate buffer (pH 5.0, 0.1M); 0.1 mL of HRP (10 ng/mL) was added to start the reaction. 0.05 mL of this solution was taken every three minutes and added to 0.95 mL of phosphate buffer (pH 8.0, 1.0M) and spectra recorded. This experiment was repeated. Result: Fluorescence after 3 minutes—background fluorescence.

|   | 11 + 49 | XV + 49 | 49 |
|---|---|---|---|
| F.U. | 535 | 0.54 | 0.50 |
|   | 552 | 0.55 | 0.50 |

(b) At pH 7.0

0.01 mL of dicarboxidine 11 (or XV), 0.1 mL of 49 and 0.04 mL of $H_2O_2$ were added to 0.75 mL (0.76 mL) of phosphate buffer (0.1M, pH 7.0). 0.1 mL of HRP (100 ng/mL) was added to start the reaction and the spectra recorded. This experiment was repeated.

Results:

|   | 11 + 49 | XV + 49 | 49 |
|---|---|---|---|
| F.U. | 1760 | 220 | 40 |
|   | 1776 | 222 | 40 |

EXAMPLE 14

Sensitivity Measurements

Stock Solutions
  HRP 1 ng/mL
  $H_2O_2$ 50 Mm
  citrate buffer pH 4.5 (0.1M)
  Tris buffer pH 8.3 (1M)
  Dicarboxidine 10 mM
  51 10 mM
  48 10 mM 0.01 mL of dicarboxidine 11, 0.01 mL of 51 or 48 as the coupler, and 0.04 mL of $H_2O_2$ were added to citrate buffer (pH 4.5, 0.1M). 0.1 mL of the reaction solution was added to 0.9 mL of pH 8.3 (1M Tris buffer, final pH 8.1) and fluorescence recorded at 0, 2, and 5 minutes. The reaction was initiated by adding varying amounts of HRP as shown below in Table 2.

TABLE 2

|   | Coupler (mL) | DCD (mL) | $H_2O_2$ (mL) | HRP (ng/mL) | Buffer (pH 4.5) (mL) | *F units × 10 |
|---|---|---|---|---|---|---|
| 1. | 0.01 | 0.01 | 0.04 | 0.00 | 0.94 | 10 |
| 2. | 0.01 | 0.01 | 0.04 | 0.01 | 0.93 | 30 |
| 3. | 0.01 | 0.01 | 0.04 | 0.03 | 0.91 | 52 |
| 4. | 0.01 | 0.01 | 0.04 | 0.05 | 0.89 | 75 |
| 5. | 0.01 | 0.01 | 0.04 | 0.10 | 0.84 | 168 |
| 6. | 0.01 | 0.01 | 0.04 | 0.20 | 0.74 | 345 |

*Fluorescence Units

EXAMPLE 15

Assay for Chlamydia (1) The formulations of the solutions used in the following Example are as follows:

A. Sample Solubilization Buffer Solution: 0.1% sodium 7-thiatetradecyl sulfate, 6.5M dithiothreitol, 10 mM ethylene-diaminetetraacetic acid (EDTA) in phosphate-buffered saline, pH 7.4

B. Silica Beads Solution: 5.0% (w.v) of alkyl-silica beads in 0.2% octyl-glucoside and 0.1% bovine serum albumin in phosphate-buffered saline, pH 7.4. Alkyl silica beads include octyl-silica beads (5.0 diameter) from J. T. Baker Co., Lot #1334106, octadecyl-silica beads (3.0μ diameter) from Serva, Lot #43546.

C. Antibody Solution: Affinity purified rabbit polyclonal antisera raised specifically against *Chlamydia trachomatis* in 0.1% chenodeoxycholate, 1.0% dextran in 0.2M tris, pH 7.2.

D. Binding Partner Solution: Horseradish peroxidase-goat anti-rabbit IgG conjugate, 1.0% fish gelatin, 1.0% diethylaminoethyl-dextran (Pharmacia), 0.2 mg/mL 8-anilino-1-naphthalenesulfonic acid, 0.1 trypsin inhibiting units, and 0.01% thimerosal in phosphate-buffered saline (25 mM sodium phosphate, 150 mM sodium chloride, pH 6.6).

E. Blocking Solution: 50% Moducyte (IV) (Miles), 0.1% Tween 20, and 0.5% octyl-glucoside in Tris-buffered saline, pH 7.5.

F. Substrate Solution: Dicarboxidine (2.6 mM), gentisic acid (2.6 mM) glucose (100 mM), dextran (1% W/V, 2×10$^6$ D, Sigma, to facilitate capillary movement of the solution), in 0.1M adipate buffers (pH5.5).

G. Glucose Oxidase—Polystyrene The following preparation was performed at 4° C. 2.0 mL of a glucose oxidase solution (7.23 mg/mL, Biozyme) was diluted to 21.0 mL with saline solution (0.1M sodium chloride). This solution was dialyzed overnight against 1.0L of saline. To a suspension of carboxylated-polystyrene beads (0.88 µm) in water (28.0 mL, 1.875% w/v) 1-ethyl-3-(3-dimethylaminopropyl) carbodiimide (EDAC) (262.5 mg) was added while vortexing. The resulting suspension was incubated for 4 minutes while stirring continuously. The suspension was then added to the glucose oxidase solution previously prepared. The resulting suspension was incubated overnight on a rotator. The beads within the suspension were then collected by centrifugation (10,000 rpm for 10 minutes) and then resuspended in 35.0 mL of glycine buffer (0.17M glycine, 0.1M sodium chloride, 0.005% thimerosal, pH 9.2). The beads were then collected two more times by centrifugation and resuspended each time in 35.0 mL of the glycine buffer (with 1.0% bovine serum albumin added). The beads were then incubated in the glycine-BSA buffer for 2 hours on a rotator. The beads were then collected three more times by centrifugation and each time resuspended in 35.0 mL Tris buffer (0.2M Tris/HCl, pH 7.5) to afford glucose oxidase-beads.

(2) Stock Chlamydia elementary bodies (formaldehyde (0.1%) fixed at 10$^{10}$ IFU/mL) were placed in 1 ml of Sample Solubilization Buffer Solution. 50 µl of this solution was then combined with 35 mL of Silica Beads Solution and 15 µl of Glucose Oxidase-Polystyrene Beads to form an assay solution. The assay solution was then placed in a test well containing a glass fiber filter on top of an absorbent pad. The binding reaction was stopped by the addition to the test well of 100 µl of Blocking Solution. 50 µl of Antibody Solution was then added to the test well and allowed to incubate at room temperature for 5 minutes. The binding reaction was then stopped by the addition to the test well of 100 µL of Blocking Solution. 50 µl of Binding Partner Solution was then added to the test well and allowed to incubate for 5 minutes at room temperature. The binding reaction was then stopped by the addition to the test well of 50 µl of Blocking Solution, followed by the addition of citrate buffer (100 µL). 50 µl of Substrate Solution was then added to the test well and the resulting color read at 5 and 10 minutes. The reaction was stopped with addition of 100 µL citrate to the test well. This assay effectively detected the presence of Chlamydia bound to the surface of the silica beads.

EXAMPLE 16

Detection of Chlamydie in Clinical Sample

A clinical sample suspected of containing Chlamydia was collected on a swab. The swab was then placed in 0.5 ml of Sample Solubilization Buffer Solution (as prepared in Example 14) for 15 minutes at room temperature and then vortexed. The swab was then removed from the solution and the solution was then filtered. 50 µl of the solution was then combined with 35 µl of Silica Bead Solution (as prepared in Example 14) and 15 µl of Glucose Oxidase-Polystyrene beads (as prepared in Example 14) to form an assay solution. The assay solution was then placed in a test well containing a glass fiber filter on top of an absorbent pad. The binding reaction was stopped by the addition to the test well of 100 µl of Blocking Solution (as prepared in Example 14). 50 µl of Antibody Solution (as prepared in Example 14) was then added to the test well and allowed to incubate at room temperature for 5 minutes. The binding reaction was then stopped by the addition to the test well of 100 µl of Blocking Solution. 50 µl of Binding Partner Solution (as prepared in Example 14) was then added to the test well and allowed to incubate for 5 minutes at room temperature. The binding reaction was then stopped by the addition to the test well of 50 µl of Blocking Solution, followed by the addition of citrate (100 µl). 50 µl of Substrate Solution was then added to the test well and the resulting color read at 5 and 10 minutes. The reaction was stopped with addition to the test well of 100 µl citrate buffer. This assay effectively determined the presence of Chlamydia bound to the surface of the solid support as an indication of the presence of Chlamydia in the clinical sample.

EXAMPLE 17

Assay for HIV Antibodies

A. Materials

Reagents. All reagents were obtained from Sigma Chemical Co. (St. Louis, Mo.) unless otherwise noted.

HIV Antigen. The recombinant antigen CBre3 was obtained from Cambridge BioScience (Worcester, Ma.), as a 6 mg/mL suspension bound to 0.9 µ diameter polystyrene latex beads. The suspension was diluted with 10 mM glycine, 10 mM NaCl, 0.05% Tween-20, 0.2% Bovine Serum Albumin (BSA), 0.02% NaN$_3$, and 0.005% thimerosal, pH 8.2, to a concentration of 337 µg beads/mL.

Protein A-HRP Conjugate. Protein A (2.5 mg/mL, Boehringer Mannheim, Indianapolis, Ind.) was dialyzed against 100 mM 3-[N-morpholino]propanesulfonic acid (MOPS), pH 7.2, and a 1.2 mL aliquot of the dialyzed solution was incubated with 120 µL of 13.3 mM sulfosuccinimidyl 4-(N-maleimidomethyl)cyclohexane- 1-carboxylate (Pierce, Rockford, Ill.) in the same buffer for 30 minutes at 30° C. The solution was then dialyzed against 50 mM 2-[N-morpholino]ethanesulfonic acid (MES), 5 mM EDTA, pH 6.0, at 4° C. and stored cold until used.

Horseradish peroxidase (HRP), (4.9 mg/mL, Toyobo, Osaka, Japan) was dialyzed against 100 mM N-[2-hydroxyethyl]piperazine-N'-[2-ethanesulfonic acid] (HEPES), pH 8.0. A 4 mL aliquot was incubated with 400 µL of 6.25 mM N-succinimidyl 3-(2-pyridyldithio) propionate (Pierce, Rockford, Ill.) in the same buffer for 1 hr at room temperature and then dialyzed against 10 mM MES, pH 6.0. The product was reduced by adding 100 µL of 500 mM dithioerythritol (DTE) in MES. After 30 minutes, the thiolated HRP was separated from DTE on a Sephadex G-25 column buffered with 50 mM MES, 5 mM EDTA, pH 6, under argon. A 2.3 mL aliquot of the purified product was degassed and treated with 700 µl of maleimidated Protein A overnight at 4° C. Remaining reactive groups were capped by incubating with sodium 2-thioacetate (5 mM final) for 30 minutes, followed by sodium iodoacetate (25 mM final) for 30 minutes. The crude conjugate was dialyzed against 100 mM Tris, 150 mM NaCl, pH 7.4 and further purified by gel filtration on Superose 12 in 50 mM $NaH_2PO_4$, 150 mM NaCl, 0.05% $NaN_3$, pH 7.0. The conjugate was stored in 25 mM $NaH_2PO_4$, 150 mM NaCl, pH 6.6.

Cassettes. White polystyrene cassettes were injection molded by Protomold, Inc., Medford, Oreg.. Glass fiber paper GF/B (used for wicks) and absorbent paper were obtained from Whatman, Inc., Clifton, N.J.

Human IgG Beads. Human IgG (Miles Laboratories, Elkhart, Ind.) in 150 mM NaCl was clarified by centrifugation and dialyzed against 10 mM NaCl, 1 mM MES, pH 6.0, at 4° C. to give 8.9 mg IgG in 3 mL buffer.

Carboxylated latex beads (0.88μ, Seradyn, Indianapolis, Ind.) were cleaned by the mixed bed ion exchange technique, as specified by the manufacturer, and stored at 4°–8° C. in water.

The purified beads (100 mg in 1 mL of water) were mixed with 50 mg 1-ethyl-3-(3-dimethylaminopropyl)carbodiimide (EDAC) in a buffer containing 1.5 mL 10 mM NaCl, mM MES, pH 6.0, and allowed to stand for 3 minutes. This mixture was then added dropwise to the IgG solution contained in an 8 mL Oak Ridge centrifuge tube immersed in the cone of a Branson Sonifier 350 operating at 70% of maximum power. The remaining beads were rinsed into the tube with 0.5 mL of the same buffer and the suspension gently agitated overnight at room temperature. The beads were then centrifuged and again washed with the same buffer and resuspended in 5 mL of 0.17M glycine, 0.1M NaCl, and 10 mg/mL BSA at pH 9.2. After 3.5 hours at room temperature, the beads were washed with three 5 mL aliquots of 10 mM glycine, 10 mM NaCl, 0.02% $NaN_3$, 0.005% thimerosal, 0.2% BSA, 0.05% Tween 20, pH 8.2, resuspended in the same buffer at 12.5 mg/mL, and stored refrigerated.

Glucose Oxidase Beads. A 21 mL solution of 14.5 mg glucose oxidase (Biozyme, Blaenavon, South Wales, Great Britain) was prepared by dialysis against 0.1M NaCl, pH~6. After incubation of the cleaned carboxylated beads (525 mg) with 262.5 mg EDAC in 28 mL of water with stirring for 4 minutes, the glucose oxidase solution was added and the mixture was agitated overnight at room temperature. The product was purified in the manner described for the human IgG beads except that the final wash buffer was 0.2M Tris/HCl, pH 7.5, and the final bead concentration was 15 mg/mL.

Substrate. A solution containing, per liter, 2.6 mmol of dicarboxidine (Kabi Vitrum, Stockholm, Sweden), 2.6 mmol of 2.5-dihydroxybenzoic acid, 100 mmol glucose, 10 mg of dextran ($2\times10^6$ D, Sigma), and 100 mmol of adipic acid, pH 5.5, was prepared fresh daily.

Samples. Positive samples and negative controls that were confirmed by Western blot were obtained from Epitope, Inc., Beaverton, Oreg. Additional negatives were obtained from the American Red Cross (Peninsula Memorial Blood Bank, Burlingame, Calif.). Sample (serum or blood) was diluted 1:10 in 10 mM Tris, 155 mM NaCl, 0.3% Tween 20, 0.5% Nonidet P-40 (NP-40, Sigma), pH 7.4, with or without 31.2 μg glucose oxidase beads per 100 μL, depending on whether these beads were preincorporated in the glass fiber wick.

B. Methods.

Preparation of Strips with IgG Control Beads, Glucose Oxidase Beads, and Antigen Beads Predried Thereon. Suspensions of 4 μg of human IgG beads in 50 μL of storage buffer (a), 31 μg of glucose oxidase beads in 100 μL of 20.2M Tris, pH 7.5(b), and 33 μg of HIV antigen beads in 50 μL of 10 mM glycine, 10 mM NaCl, 2.5% (w/v) mannitol, 0.05% Tween 20, 0.02% $NaN_3$, and 0.005% thimerosal, pH 8.2(c), were spotted onto different areas of an untreated glass fiber strip, where (a) was spotted at one end, (b) at the other end and (c) in the middle. The strip was dried for 10 minutes at 65° in a tunnel drier and stored with a desiccant until used.

C. Assay Procedure.

1. Sample (100 μL) in diluent was added to the strip at the location of (b). Timing was started, and sample was allowed to wick in (60–90 seconds) in the direction of the location of (a).

2. Substrate (400 μL) was contacted with the strip at an end portion near the location of (b).

3. Conjugate (100 μL) was immediately added to the strip at the location of (c).

4. Color development at the location of (c) and (a) was observed between 10–15 minutes after initiation of timing.

D. Results.

Sera positive for HIV antibodies caused development of a blue-grey spot in the read area at the location of (c) within about 7 minutes. After 10 minutes, the spot became nearly black. Negative sera produced no change from the white background for at least 20 minutes after which a light grey color appeared in some instances. The test results were read visually.

EXAMPLE 18

Preparation of Compound 56

1.97 g of the sodium salt of p-nitrophenol(0.01 mol), 2.16 ml of dibromoethane (0.025 mol) and 0.5 g of potassium carbonate were taken in 50 ml of dry acetone (4A activated molecular sieves) and refluxed overnight. Potassium carbonate was filtered and the solvent was removed by rotary evaporation to yield 4-(2-bromoethoxy)nitrobenzene (L) in almost quantitative yield.

$^1$H-NMR: CDC1: γ 3.65 (t,2H), 4.4 (t,2H), 7.0–8.3 (ABq, 4H)/

2.46 g of ≦(0.01 mol) was dissolved in 25 ml of methanol, 5 ml of 37% formaldehyde solution was added. The reaction mixture was hydrogenated under paar apparatus at 60 psi for 4 hours at which time TLC (ethyl acetate) indicated the complete disappearance of starting material. The catalyst was filtered and the filtrate mixed with 500 ml of ethyl acetate and washed with water (5×50 ml). The solvent was removed by rotary evaporation and the product was purified by column chromatography ($SiO_2$, 230–400 mesh, methylene chloride) to yield 1.95 g of pure product 4(2-bromoethoxy)-N,N-dimethylaniline (M).

Yield 80%. $^1$H-NMR:$CDCl_3$:δ:2.85(S,6H). 3.6(t,2H), 4.25(t,2H), 6.8(ABq4H).

0.39 g of acridone (0.002 mol) and 0.06 g of sodium hydride (0.0025 mol, dry powder, 90%) were taken in 10 ml of dry DMF (CaH, dry) and stirred under argon at 50° C. for 2 hours. At this point the temperature of the oil bath was increased to 80° C. and 0.488 g of M (0.002 mol) was added slowly over 20 minutes. The reaction mixture was stirred under argon for 6 hours at 80° C., at which time TLC (ethyl acetate) indicated the absence of M, therefore the reaction was quenched with water (100 ml), neutralized with dilute acid and the product was extracted into ethyl acetate (50 ml×5). The ethyl acetate fraction was washed with water (50×3), dried over sodium sulphate. The solvent was removed by rotary evaporation and the product was purified by column chromatography ($SiO_2$, 230–400 mesh, methylene chloride:ethyl acetate) to yield 0.23 g of pure product 10 O-(4-N,N-dimethylanilinoethyl)acridone (56).

Yield 64% $^1$H-NMR:CDCl$_3$:γ:1.85(S,6H). 4.4(t,2H), 4.8(t,2H), 6.8(ABq4H), 7.2-7.8(m, 6H) 8.6 (d,d,2H). I.R.: Nujol:cm$^{-1}$: 2980(m), 1600(m), 1590(m).

EXAMPLE 19

Preparation of Compound 57

36 mgs of 56 (0.1 mmol prepared in Example 18) was taken in 10 ml of dry THF under argon at 5° C. At this point excess of borane in THF (2 ml of 1M solution) was added. The reaction mixture turned bright yellow and was slowly allowed to warm to room temperature over 2 hours. The reaction mixture was added to 50 ml ethyl acetate and washed with brine (5×10 ml). The solvent was removed by rotary evaporation and the product was purified on a preparative TLC plate (silica gel 1000 microns, methylene chloride) 26 mgs of pure product N-(N,N-dimethylanilinoethyl)dihydroacridine (N) was isolated.

Yield 76% $^1$H-NMR:CDCl$_3$:γ:2.8(S,6H), 3.95(S,2H), 4.3(broad S, 4H), 6.7–7.3(m,12H).

Since N undergoes air oxidation, it was immediately carried over to the next reaction.

69 mgs of N (0.2 mmol) was dissolved in 2 ml of acetonitrile (CaH, dry) under argon in an ice bath. 66 mgs of trityl tetrafluoroborate (0.2 mmol) was dissolved in 1 ml of dry acetonitrile and added to 12 slowly over 2 minutes. The reaction mixture was allowed to stir for 10 minutes at which point acetonitrile was removed by rotary evaporation, the green paste was washed with hexane (3×10 ml). the green paste was now applied to a C-18 reverse phase column and eluted with acetonitrile/water (1:9) 7.7 mgs of pure product N-(N,N-dimethylanilinoethyl)acridinium tetrafluoroborate) 57 was collected and dried. 57 was recrystallized from water as yellow needles.

Yield 89%. M.P.: 142°–143° C. Mass spectrum:FAB: M+: 343. $^1$H- NMR:CD$_3$CN:γ:2.98(S,6H), 4.74(t,2H), 5.78(t,2H) 6.65–7.15(ABv4H), 7.92 (d,d,2H), 8.46(d,d,2H), 8.5(d,2H), 8.72(d,2H), 9.9(S,1H). I.R.: THF:cm$^{-1}$:2980(m), 1620(m), 1500(m), 1440(S), 1370(S). UV(pH 5.0 citrate buffer 0.1M) 357.6 nm (18800) 420 nm (4000)

EXAMPLE 20

Preparation of Compound 54

5.5 g of hydroquinone (0.05 mol) and 3.42 g of benzyl bromide (0.02 mol) along with 1 g of pottasium carbonate were refluxed in dry acetone (dried over 4 Å activated molecular sieves) for 24 hours. The reaction mixture was poured into 500 ml of water, neutralized with dilute acid and extracted into methylene chloride (5×50 ml). The solvent was removed by rotary evaporation and the product was purified by column chromatography (SiO$_2$, 230–400 mesh, methylene chloride) to yield 3.6 g of product 4-benzyloxyphenol (P).

Yield 90% based on benzyl bromide. $^1$H-NMR:CDCl$_3$:γ:5.0(S,3H), 6.8(ABv,4H), 7.45(m,5H).

2 g of P (0.01 mol) and excess of 1,2-dibromoethane (5 g) were taken in 100 ml of dry acetone (dried over 4A activated molecular sieves) containing 1 g of potassium carbonate. The reaction mixture was refluxed under argon for 48 hours at which time potassium carbonate was filtered and acetone was mixed with 500 ml of ethyl acetate and washed with water (5×50 ml). The solvent was removed by rotary evaporation and the product was purified by column chromatography (SiO$_2$, 230–400 mesh, methylene chloride) to yield 2.6 g of product 4- benzyloxy-1-(2-bromoethoxy)benzene (Q)

Yeild 85%. $^1$H-NMR:CDCl$_3$:γ:3.6(t,2H), 4.2(t,2H), 5.0(S, 2H) 6.8 (ABq,4H), 7.4(m,5H).

0.39 g of acridone (0.002 mol) and 0.06 g of sodium hydride (0.0025 mol, dry powder, 90%) were taken in 10 ml of dry DMF (CaH, dry) and stirred under argon at 50° C. for 2 hours. At this point, the temperature of the oil bath was increased to 90° C. and 0.614 g of Q (0.002 mol) was added slowly over 20 minutes. The reaction mixture was stirred under argon for 6 hours at 90° C., at which time TLC (ethylacetate) indicated the absence of Q; therefore, the reaction was quenched with water (100 ml), neutralized with dilute acid and the product was extracted into ethyl acetate (50 ml×5). The ethyl acetate fraction was washed with water (50 ml×3), dried over sodium sulphate. The solvent was removed by rotary evaporation and the product was purified by column chromatography (SiO$_2$, 230–400 mesh, methylene chloride: ethyl acetate (5:1)) to yield 0.24 g of pure product N-(benzyloxyphenoxyethyl)acridone (R).

Yield 56% $^1$H-NMR:CDCl$_3$:δ:4.4(t,2H), 4.8(t,2H), 5.0(S, 2H) 6.9 (ABv,4H), 7.4–8.0(m,8H), 8.5(d,d,2H). I.R.: Nujol:cm$^{-1}$: 2980(m), 1600(S), 1500(m), 1490(m).

0.084 g of R (0.2 mmol) was dissolved in 5 ml of ethanol and 2 ml of acetone, 0.005 g of Pd/C (10%) was added to it and the solution is hydrogenated under paar apparatus at 20 psi for 4 hours, at which time TLC (methylene chloride) indicated the complete disappearance of starting material. The catalyst was filtered and the solution is taken in 200 ml of ethyl acetate and washed with brine (50 ml×5). The solvent was removed by rotary evaporation and the product was purified on a preparative TLC plate (silica gel, 1000 microns, ethyl acetate) to yield 0.05 g of pure product N-4-hydroxyphenoxyethylacridone Yield 76%. $^1$H-NMR:CDCl$_3$:γ:4.4(t,2H), 4.8(t,2H), 6.7 (ABq,4H), 7.6–8.0(m,6H), 8.5(d,d,2H). I.R.: Nujol:cm$^{-1}$: 3400(w), 2980(m), 1620(m), 1590(m), 1500(m).

EXAMPLE 21

Preparation of Compound 55

33 mgs of 54 (0.1 mmol) (prepared in Example 20) was taken in 10 ml of dry THF under argon at 5° C. At this point excess of borane in THF (2 ml of 1M solution) was added. The reaction mixture turned bright yellow and was slowly allowed to warm to room temperature over 2 hours. The reaction mixture was added to 50 ml ethyl acetate and washed with brine (5×10 ml). The solvent was removed by rotary evaporation and the product was purified on a preparative TLC plate (silica gel, 1000 microns, methylene chloride). 24 mgs of pure product N-4-hydroxyphenoxyethyldihydroacridine (S) was isolated.

Yield 75%. $^1$H-NMR:CDCl$_3$:γ:3.95(S,2H), 4.3(broad S,4H), 6.7–7.3 (m, 12H) .

As the product (6) undergoes air oxidation, it was immediately carried over to the next reaction.

I.R.: THF:cm$^{-1}$: 3500(m), 2980(m), 2900(m), 1620(m), 1500(s), 1440(s), 1360(s). UV (pH 5.0 citrate buffer 0.1M): 357 nm (13600) 420 nm (2700).

32 mgs of S (0.1 mmol) was dissolved in 2 ml of acetonitrile (CaH, dry) under argon in an ice bath. 33 mgs of trityl tetrafluoroborate (0.1 mmol) was dissolved in 1 ml of dry acetonitrile and added to S slowly over 2 minutes. The reaction mixture was allowed to stir for 10 minutes at which point acetonitrile was removed by rotary evaporation, the green paste was washed with hexane (3×10 ml). the green paste was applied to a C-18 reverse phase column and eluted with acetonitrile/water (1:9). 35 mgs of pure product N-(4-hydroxyphenoxyethyl)acridinium tetrafluoroborate 55 was collected and dried. 7 was recrystallized from water as dark yellow needle shaped crystals.

Yield 87%. M.P.: 267°–268° C. Mass spectrum: FAB M+-316 $^1$H-NMR: (CD$_3$CN):δ:4.66(t,2H), 5.73(t,2H), 6.5(S,1H, phenolic O-H), 6.6(ABq,4H), 7.98(d,d,2H), 8.42(d,d,2H), 8.52(d,2H), 8.72(d,2H), 9.9(S,1H).

EXAMPLE 22

Preparation of Compound 63

0.41 g of 2-carboxy-4-hydroxynaphthol (0.02 mol), 0.4 g of tert-butyl bromoacetate (0.021 mol), 0.045 g of benzyl-triethylammonium bromide (0.002 mol) and 0.12 g of sodium hydroxide (0.03 mol) were taken in 50 ml of methylene chloride and 50 ml of water and stirred at room temperature under argon for 8 hours. The reaction mixture turns dark red at the end of 8 hours. The solution is neutralized with dilute hydrochloric acid (3N), extracted into ethyl acetate (50 ml×5), the ethyl acetate layer is dried and removed by rotary evaporation. The red semisolid obtained in this fashion is taken in neat TFA (5 ml) and stirred at room temperature for 2 hours. At this time TFA was removed by rotary evaporation and the product was purified by column chromatography (SiO$_2$, 230–400 mesh, ethyl acetate) to yield 0.058 g of product 2-carboxy-4-carboxymethoxynaphthol 63.

Yield 11% $^1$H-NMR: (CD$_3$CN):γ:4.6(S,2H), 7.4–8.5(m, 5H) I.R.: Nujol:cm$^{-1}$: 3300(w), 1660(m), 1580(m).

EXAMPLE 23

Preparation of Compound 62

0.222 g of 2-carboxy-4-chloronaphthol (0.001 mol), 0.11 g of N-hydroxysuscinimide (0.0011 mol) and 0.25g of dCC (0.0012 mol) were taken in 5 ml of dry THF and stirred at room temperature for 3 hours at which time TLC (methylene chloride) indicated the total disappearance of A. The precipitated solid (urea) is filtered off, washed with 2 ml of dry THF and the combined THF solution is added to 1 g of glycine in 10 ml of water, the pH of the aqueous solution was already adjusted to 8.5 with bicarbonate. the reaction mixture was stirred overnight at room temperature. 100 ml of water is added to stop the reaction. The product is then extracted into ethyl acetate (50 ml×5), the ethyl acetate layer is dried and removed by rotary evaporation. The product was purified by column chromatography (SiO$_2$, 230–400 mesh, ethyl acetate) to yield 0.12 g of product 2-(N-carboxymethyl carboxamido)-4-chloronaphthol 62.

Yield 44%. $^1$H-NMR: (CD$_3$CN):γ:4.3(S,2H), 7.5–8.5(m, 5H) I.R.: Nujol:cm$^{-1}$: 3300(w), 1640(m), 1600(m).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of determining a peroxidase, which method comprises contacting a medium suspected of containing a peroxidase with (a) a hydroperoxide (b) a benzidine wherein at least one amino group of said benzidine is a primary amine and at least one substituent positioned ortho thereto is a hydrogen atom;

(c) and a coupler selected from the group consisting of

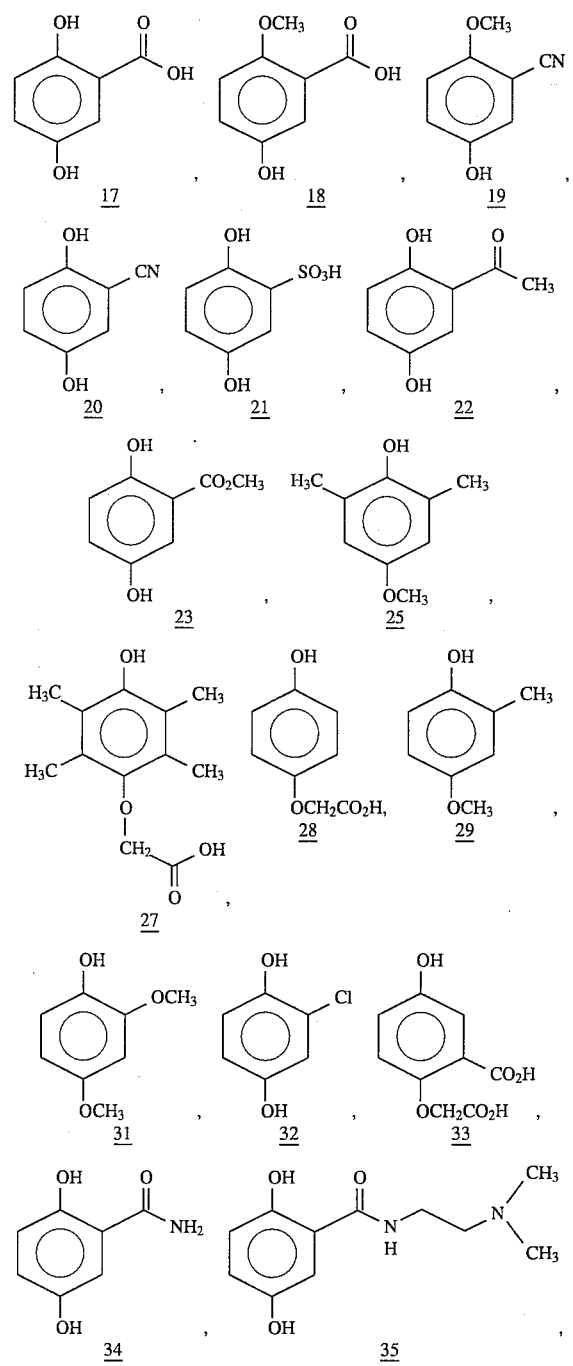

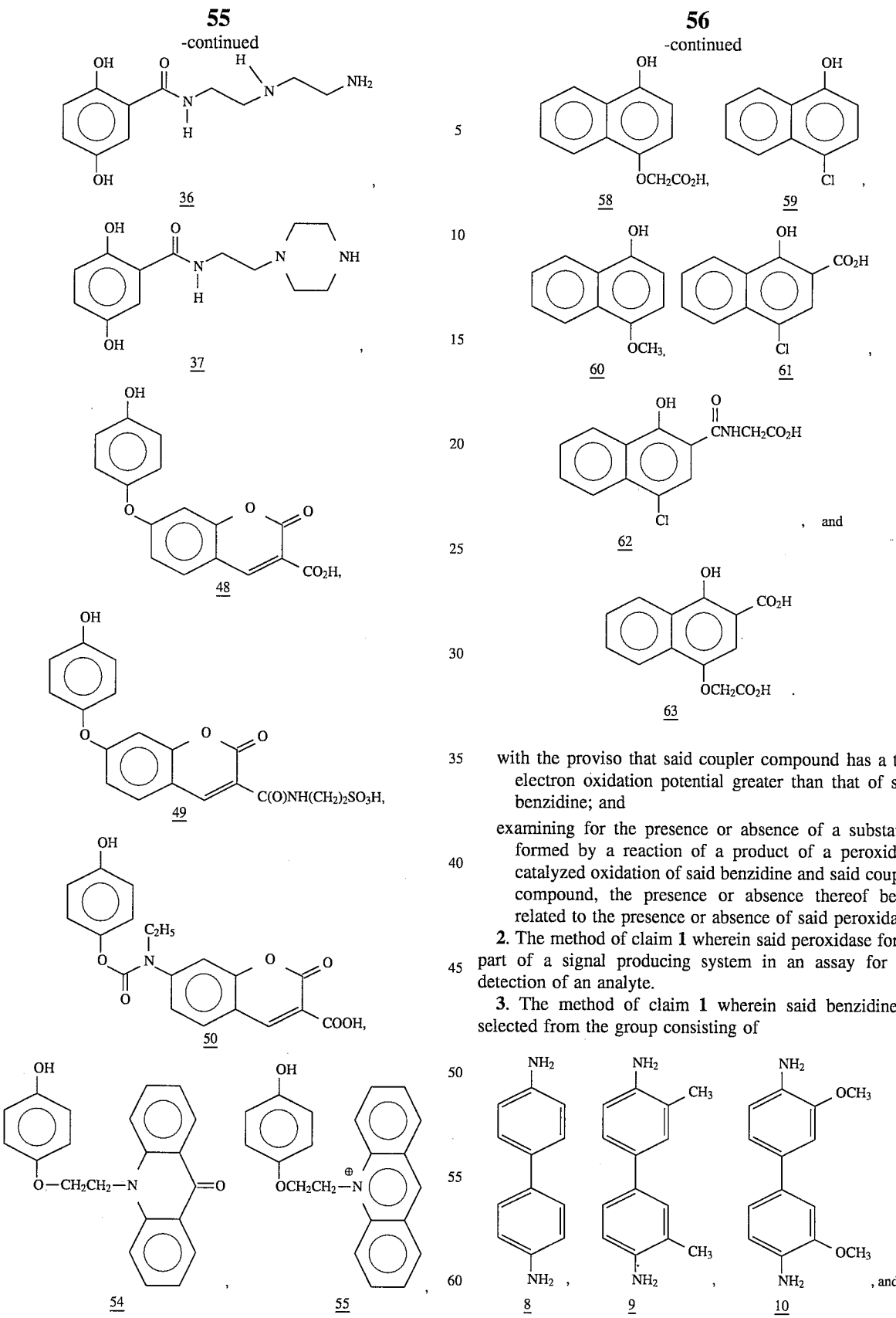

with the proviso that said coupler compound has a two electron oxidation potential greater than that of said benzidine; and examining for the presence or absence of a substance formed by a reaction of a product of a peroxidase catalyzed oxidation of said benzidine and said coupler compound, the presence or absence thereof being related to the presence or absence of said peroxidase.

2. The method of claim 1 wherein said peroxidase forms part of a signal producing system in an assay for the detection of an analyte.

3. The method of claim 1 wherein said benzidine is selected from the group consisting of

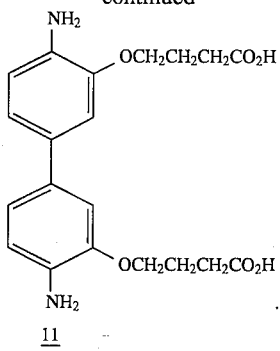

4. The method of claim 1 wherein said substance examined for is a condensation product of said product and said coupler.

5. The method of claim 1 wherein said substance examined for is a chromophor.

6. A kit for examining for the presence or absence of peroxidase activity, said kit comprising in packaged combination:

(a) a hydroperoxide;

(b) a benzidine wherein at least one amino group of said benzidine is a primary amine and at least one substituent positioned ortho thereto is a hydrogen atom;

(c) a coupler selected from the group consisting of

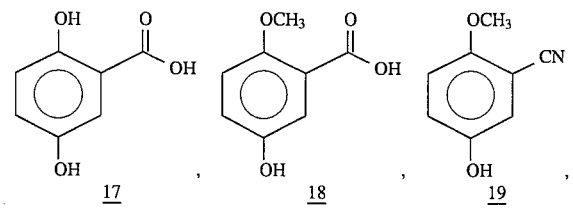

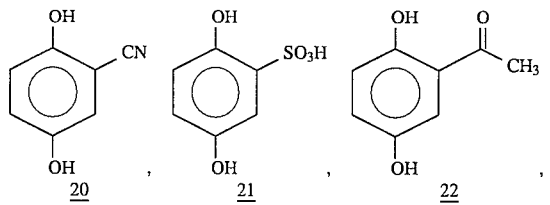

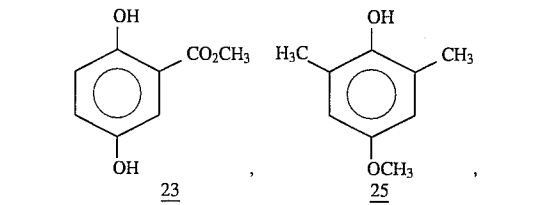

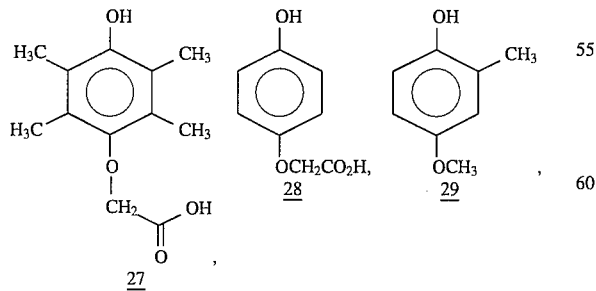

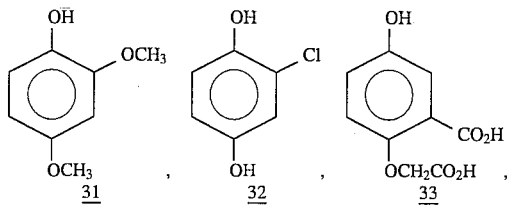

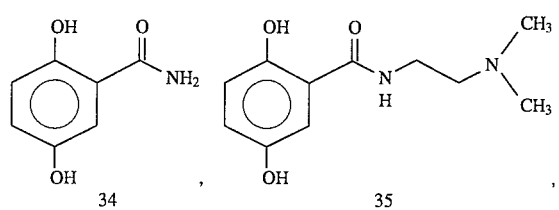

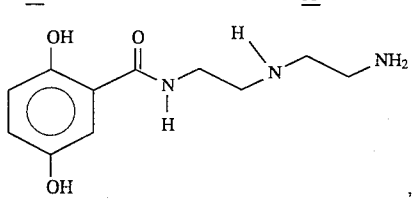

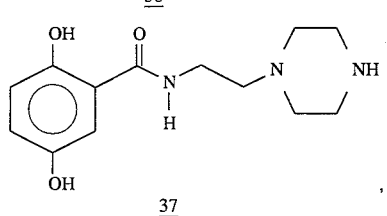

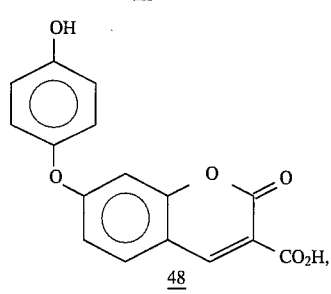

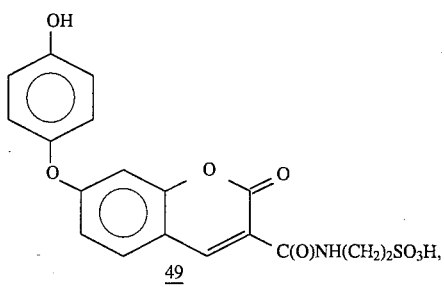

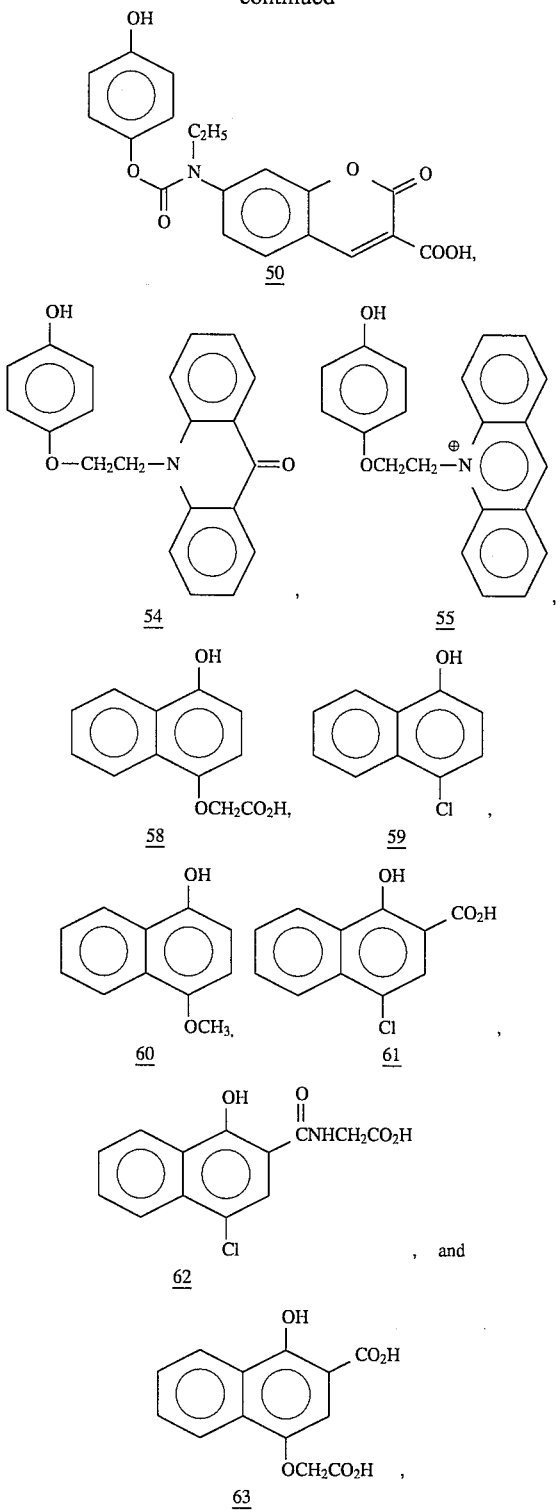

(d) a member of a specific binding pair (sbp) conjugated to a peroxidase enzyme.

7. The kit of claim 6 wherein said benzidine is selected from the group consisting of:

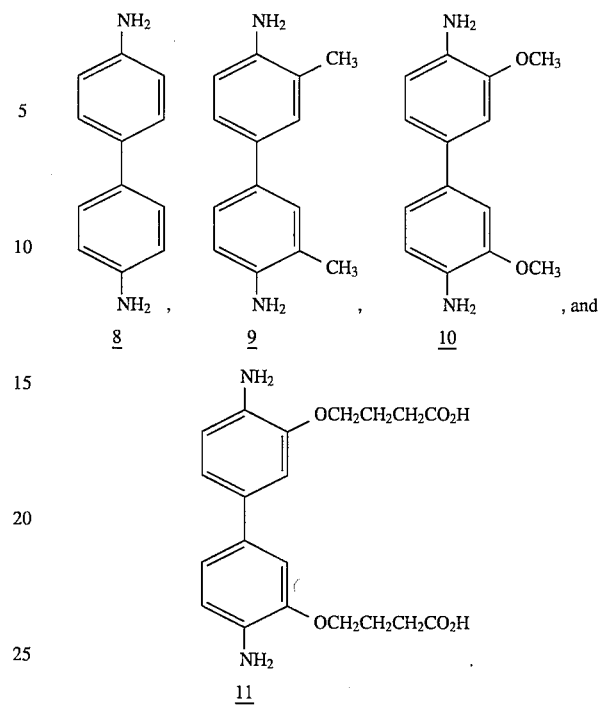

8. A kit of claim 6 wherein said peroxidase enzyme is horseradish peroxidase.

9. A kit of claim 6 wherein said sbp member is a ligand or a receptor.

10. A kit of claim 6 wherein said sbp member is an antibody, an antigen, or a ligand analog.

11. An assay for an analyte which is a member of a specific binding pair (sbp), which assay comprises:

combining a medium suspected of containing said analyte, a first sbp member that binds said analyte, and a peroxidase enzyme conjugated to a second sbp member, wherein said second sbp member binds to said analyte or to said first sbp member when said second sbp member is an analyte analog to form a complex, and examining for the presence or absence of activity of said peroxidase enzyme in said complex by treating said peroxidase enzyme with a hydroperoxide, a benzidine wherein at least one amino group of said benzidine is a primary amine and at least one substituent positioned ortho thereto is a hydrogen atom, and a coupler selected from the group consisting of:

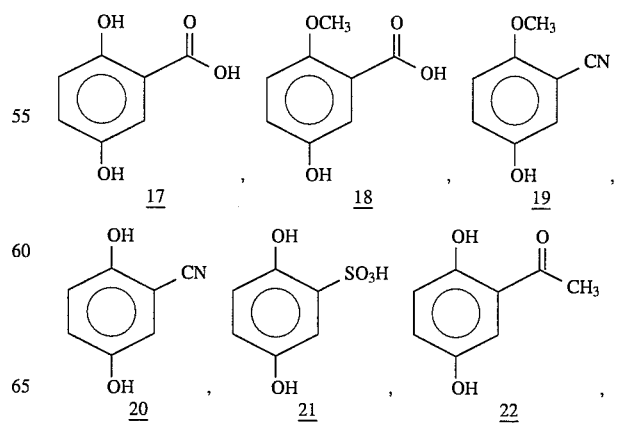

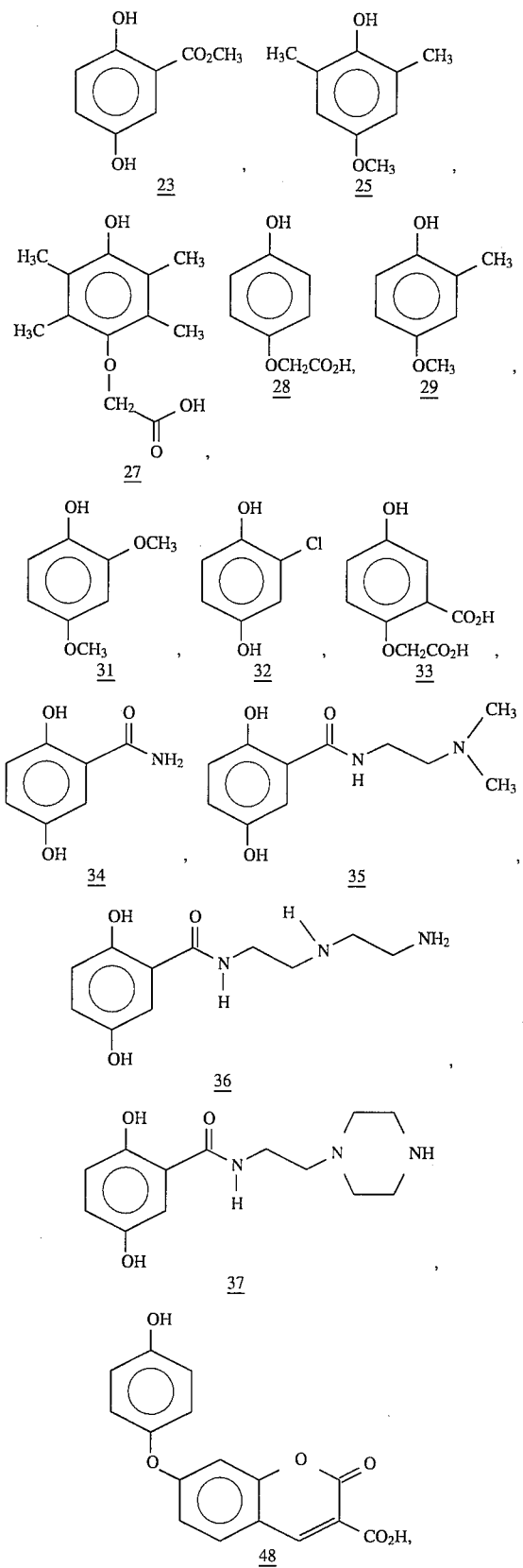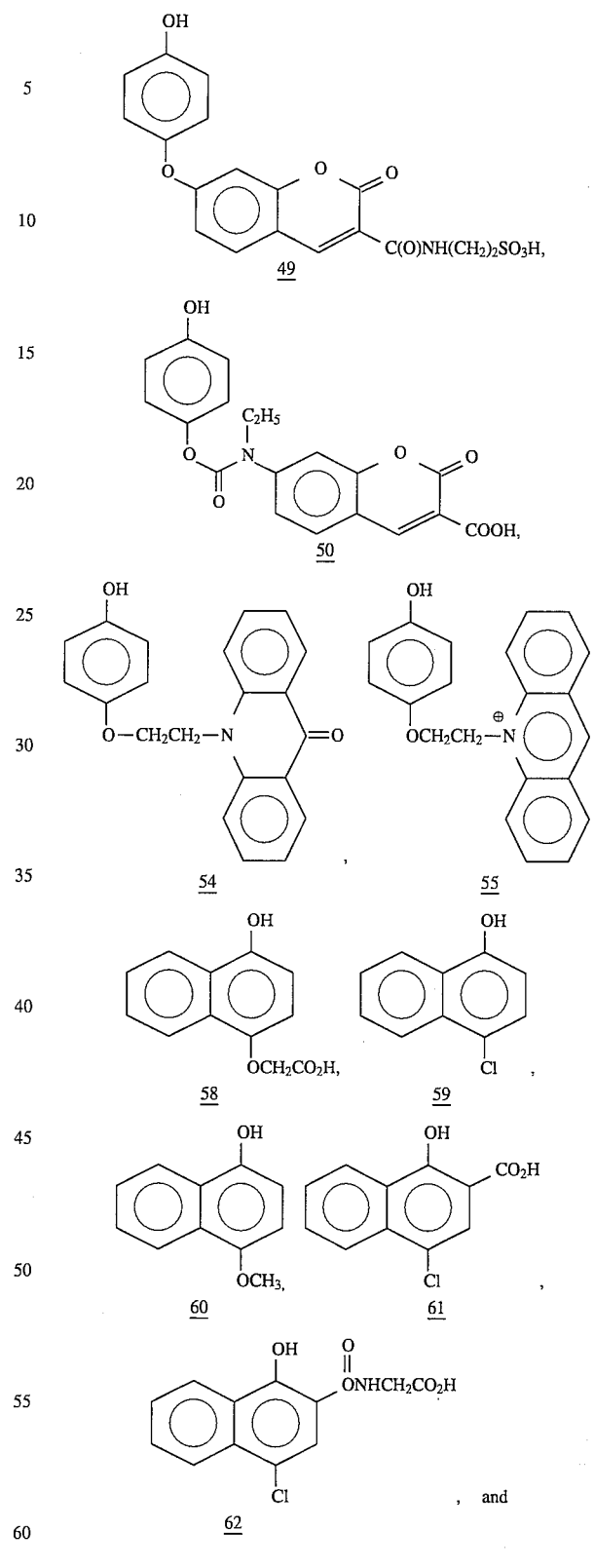

-continued
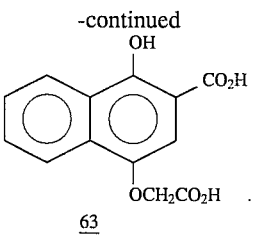
63
12. The assay of claim 11 wherein said first sbp member is insolubilized and is a receptor for said analyte and said second sbp member is a receptor for said analyte.
13. The assay of claim 11 wherein said second sbp member is an analyte analog and said first sbp member is a receptor for said analyte and said analyte analog.
* * * * *